US006610638B1

(12) United States Patent
Tanigawa et al.

(10) Patent No.: US 6,610,638 B1
(45) Date of Patent: Aug. 26, 2003

(54) HIGH PURITY 1,3-PROPANEDIOL DERIVATIVE SOLVENT, PROCESS FOR PRODUCING THE SAME, AND USE THEREOF

(75) Inventors: Hiroto Tanigawa, Ohtake (JP); Hiroto Miyake, Ohtake (JP); Hiroshi Koyama, Hidaka (JP); Akihiko Fujita, Tokyo (JP); Katsuya Maruo, Ohtake (JP)

(73) Assignee: Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 09/701,663
(22) PCT Filed: Mar. 30, 2000
(86) PCT No.: PCT/JP00/02043
§ 371 (c)(1),
(2), (4) Date: Nov. 30, 2000
(87) PCT Pub. No.: WO00/58252
PCT Pub. Date: Oct. 5, 2000

(30) Foreign Application Priority Data

Mar. 31, 1999 (JP) ............................................. 11-092842
Oct. 25, 1999 (JP) ............................................. 11-301907

(51) Int. Cl.$^7$ .............................................. C07C 45/00
(52) U.S. Cl. ..................... 510/171; 568/465; 560/224; 203/44
(58) Field of Search ............................... 560/190, 224, 560/263; 554/149; 203/44, 51; 568/465

(56) References Cited

U.S. PATENT DOCUMENTS

| | | | | |
|---|---|---|---|---|
| 1,976,677 A | * | 10/1934 | Wittwer | |
| 2,495,313 A | | 1/1950 | Bludworth | ............... 260/615 |
| 4,544,453 A | * | 10/1985 | Gupta | |
| 4,699,998 A | * | 10/1987 | Green | |
| 5,239,111 A | * | 8/1993 | Chu et al. | |
| 5,334,778 A | | 8/1994 | Haas et al. | ............... 568/862 |
| 5,723,024 A | * | 3/1998 | Berg | |
| 6,239,315 B1 | * | 5/2001 | Muller et al. | |
| 6,531,635 B1 | * | 3/2003 | Yoshitome et al. | ......... 568/465 |

FOREIGN PATENT DOCUMENTS

| | | |
|---|---|---|
| EP | 0572812 | 1/1998 |
| JP | 6348002 | 12/1994 |
| JP | 7025821 | 1/1995 |
| JP | 8291097 | 5/1996 |
| JP | 10010711 | 1/1998 |
| WO | WO 98/50339 | 4/1998 |

OTHER PUBLICATIONS

Industrial Solvents Handbook, Fifth Edition, Ernest W. Flick, 1998.*
ASTM Standard D–4773–93, Web Page description of Standard and ASTM report of the history of this standard, Jun. 10, 1998.*
International Search Report for PCT/JP00/02043, 2001.

* cited by examiner

Primary Examiner—Gregory E. Webb
(74) Attorney, Agent, or Firm—Morgan & Finnegan, L.L.P.

(57) ABSTRACT

The present invention No. I is to obtain a high purity 3-alkoxy-1-propanol having the content of alcoholic impurities of not more than 0.3% by weight by allowing to react acrolein with a linear or branched alcohol having a carbon number of 1–4 using acrolein having the content of propionaldehyde of not more than 1% by weight as a raw material, a 3-alkoxy-1-propanol is produced by a hydrogenation reaction using hydrogen of a reaction mass under the presence of a catalyst, followed by recovering through a distillation of the 3-alkoxy-1-propanol having the content of alcoholic impurities of not more than 0.3% by weight from a crude solution in the hydrogenation reaction.

7 Claims, 1 Drawing Sheet

HIGH PURITY 1,3-PROPANEDIOL DERIVATIVE SOLVENT, PROCESS FOR PRODUCING THE SAME, AND USE THEREOF

TECHNICAL FIELD

The present invention No. I relates to a high purity 3-alkoxy-1-propanol, particularly, a high purity 3-methoxy-1-propanol, in which acrolein and an alcohol, particularly, methanol are employed as raw materials, and a method for the preparation thereof.

The present invention No. II relates to a cleaning agent for lithography which is employed for dissolving or removing a resist, etc., and in more detail, a cleaning agent for lithography which can be usefully employed for cleaning a coating apparatus such as an inside of a coater cup, for removing an unnecessary resist in coating the resist or on a base plate after coating, for removing a resist from the base plate after attaining use purpose of the resist, and for cleaning and rinsing the base plate after removing a resist.

The present invention No. III relates to a rinsing liquid for lithography and, in more detail, it relates to a rinsing liquid for lithography which is useful for dissolving or removing cured and uncured unnecessary resist and a reflection protecting-layer from an integrated circuit element, a color filter, a base plate for a liquid crystal display element, etc., or coating apparatus for a resist, etc.

The present invention No. IV relates to a solvent for a resist composition which is employed as an object for irradiating a corpuscular beam such as an ultraviolet ray, a far ultraviolet ray, an X-ray, and an electron beam, etc., and relates to a resist composition characterized by the use thereof and, in more detail, it relates to a solvent which provides resist composition which is excellent in safeness during the use, coatability, residual ratio of a layer during development, uniformity of line width of a pattern after development, and resist adhesion during development, and it relates to a resist composition composed of the solvent and a resist resin.

The present invention No. V relates to a photo-curable resin composition which is preferred as an etching resist or a solder resist which is employed in, particularly, a preparation stage of a printed circuit board.

BACKGROUND ART 3-methoxy-1-propanol is also named 1,3-propane diol methylether, and it has an alcoholic hydroxyl group and methyether group. The alcoholic hydroxyl group has esterification reactivity, etherification reactivity, and halogenation reactivity, and it is an important compound as many useful compounds, particularly, raw materials for medicines and agricultural chemicals, and functional solvents.

In the case that a variety of reactions are conducted using 3-methoxy-1-propanol, if alcoholic impurities are contained in 3-methoxy-1-propanol, since a reaction of the alcoholic impurities also proceeds under same reaction conditions as in 3-methoxy-1-propanol, compounds derived from the alcoholic impurities end to be contained in a final product obtained. This causes a serious problem in the case that 3-methoxy-1-propanol is employed as, particularly, a raw materials for medicines and agricultural chemicals, and functional solvents.

As a method for the preparation of 3-methoxy-1-propanol, for example, U.S. Pat. No. 2,495,313 describes a method in which methanol and acrolein are employed as raw materials, and JP-A-08113546 Official Gazette describes a method in which methanol and 3-chloro-1-propanol are employed as raw materials. However, there are not described the amount of the alcoholic impurities contained in 3-methoxy-1-propanol at all.

JP-A-07025821 Official Gazette describes a method for the preparation of 3-methoxy-1-propanol by hydrogenation of a product obtained by allowing to react methanol with acrolein under the presence of a basic catalyst, followed by allowing to react with acetic acid under the presence of an acidic catalyst, and a solvent containing thereof. Further, JP-A-10306050 Official Gazette describes an etheralcohol-based solvent containing 3-methoxy-1-propanol, however, there is only obtained a product having purity of 98.4% or so, a kind and amount of the impurities are not described in all the prior arts and, the prior arts are not aware a problem by the impurities.

In the preparation of an integrated circuit element, a color filter, a liquid crystal display element, and a printed circuit board, etc., fine processing is demanded and, in order to satisfy the demand, there has been conventionally employed a lithography technology using a resist.

As a conventionally well known or publicly-known resist, there have been employed a screen ink, dry-film resist, electrodeposition resist, and liquid resist, etc., and, of those, there has been recently attention to the liquid photoresist. The liquid photoresist includes a positive type one and a negative type one.

In the liquid photoresist compared to the dry-film resist, since the thickness of resist coating layer can be thinned as well as in the electrodeposition resist, identical or more excellent dissolution can be expected as in the electrodeposition resist in formability of a micro-pattern. Further, a bath control is not required as in the electrodeposition resist, and since it can become more decreased in price from a viewpoint of plant investment than in the electrodeposition resist, it is hopeful as a preparation method of a micro-pattern.

As solvents to be employed for the resist composition, a variety of solvents have been conventionally known, and an appropriate solvent is selectively employed in consideration of solubility to a resist, coatability, sensitivity, developability, and properties of a pattern formed. On the other hand, independently upon a performance such as resist-forming properties, many solvents usually include a problem in view of safeness to human bodies. It is actual circumstances that the safeness to human bodies, particularly, recently becomes attached importance, and solvents are selected also in consideration of the safeness to human bodies. For example, although ethylene glycol monoethylether acetate has been known as a solvent which is excellent in the properties such as solubility, coatability, resist forming ability, it has not become quite employed as a solvent for resist after indication of a problem of the safeness to human bodies, and there has become mainly employed propylene glycol monoethylether acetate, etc., instead of that as a solvent having safeness (for example, JP-B-91001659, JP-B-92056973, and JP-B-92049938 Official Gazettes). Further, as solvents having safeness, ethyl lactate and methyl-n-amylketone, etc. are known other than propylene glycol monomethylether acetate. However, the solvents which are regarded as a solvent having high safeness compared to ethylene glycol monoethylether acetate include a problem that there are not sufficient properties such as a resist-forming ability and solubility to resist materials. For example, in the case of propylene glycol monomethylether acetate, there have been problems of the ratio of remaining solvents in a coating layer after coating a resist onto a base plate, uniformity of line width, and a fall of adhesion of a resist layer during development. This is caused by that although propylene glycol monomethylether acetate itself is a solvent having quick evaporation rate, in the case that it is employed as a solvent for a resist composition, evaporation proceeds at a coating surface alone and a so-called ultra-thin layer is formed at the surface, whereby, it becomes difficult for the solvent remained in an inside of coating surface to evaporate.

Still further, it is known that propylene glycol monomethylether acetate is poorer in solubility to a resin and an initiator compared to ethylene glycol monoethylether acetate.

Also, JP-A-06324483 and JP-A-06324499 Official Gazettes disclose a technology for improving solubility to a resin and an initiator, etc. using a β-type propylene glycol monoalkylether acetate (that is, 1-alkoxy-2-propanol acetate). However, the propylene glycol-based solvents are still insufficient in view of solubility to a resin and an initiator because of the presence of substituted groups at 1,2-position. For that reason, there has been desired a solvent in which safeness is high, which is excellent in solubility to a resin and an initiator, and in which performances such as resist formability are improved.

And also, in the case that a large amount of impurities are contained in solvents, there is a problem that it is difficult to obtain a resist layer having a stable quality because of different evaporation rate of the solvents.

In the preparation of an integrated circuit element, etc. using a lithography technology, the above-described resist composition is coated by a publicly-known method on a base plate such as a silicone base plate and glass base plate. After having been coated, solvents are removed by baking to prepare a resist layer and, a reflection protecting-layer is optionally formed on the resist layer, followed by exposing to a various radiation rays such as an ultraviolet ray, a far ultraviolet ray, an electron beam, and an X-ray, by optionally baking, and by developing to form a resist pattern.

After that, optionally, a baking is further conducted, followed by conducting an etching treatment, etc. of the base plate and by usually removing the resist.

Coating of the above-described resist composition is conducted by various publicly-known methods such as a spin-coating, roll-coating, reverse roll-coating, casting coating, doctor-coating, and dip-coating methods. For example, in the preparation of an integrated circuit element, the spin-coating method is mainly employed as a coating method for a resist. In the spin-coating method, a resist solution is dropped on a base plate and, the resist solution dropped is cast toward a periphery of the base plate by rotation of the base plate and, an excessive resist solution is shakenly removed from the periphery of the base plate to form a resist layer having a desired thickness.

The excessive resist solution is partially remained in a coater-cup, and it is solidified by evaporation of solvents with a lapse of time. Solidified substance becomes fine powder, and it is scattered and adheres to the resist base plate, resulting in that it causes a defect on a resist pattern. In order to prevent a phenomenon, the coater-cup must be cleaned every treatments of several or several tens base plates.

Further, in the case that a resist layer having a desired thickness is formed on a base plate by the spin-coating method, there is a drawback that the resist solution is partially turned in a back surface of the base plate, or the resist solution is remained in a larger thickness than in other portion at periphery of the base plate, so-called beads are formed. For that reason, it is required that an unnecessary resist or the beads are removed from the circumference of side surface or back surface in the base plate.

Still further, even in the case of the coating methods other than the spin-coating method, a resist occasionally adheres at an unnecessary portion as well as in the spin-coating method. Also, a resist is usually removed after conducting a treatment of a base plate by etching, and the resist is removed by dissolving using organic solvents even in a removal step. After that, the base plate in which the resist is removed is usually washed by pure water, etc. in order to prepare a surface of the base plate not stained by removing micro particles remained at surface, and it moves to a next step. Herein, in the case that a solvent for removing a resist is a water-insoluble organic solvent or an amine-based organic solvent, there is often arranged a step for rinsing by a clean water-soluble solvent without washing by the pure water immediately after a removing step. The reason is as follows. In the case that the water-insoluble organic solvent is employed as a removing solution, it is conducted in order to prevent that a resist dissolving in the solvent adheres again on the base plate, or, in the case that the amine-based organic solvent is employed as a removing solution in order to replace the water-insoluble organic solvent existing on the surface of the base plate with the water-soluble organic solvent and to smooth replacement with pure water, it is conducted in order to avoid a corrosion of a metallic base plate showing an alkaline property by remaining of the solvents in water.

And also, it is also required that a coating apparatus is cleaned in order to reuse the coating apparatus for a next preparation or in order to use as a coating apparatus for a different kind of materials after the completion of coating and, in the case of an integrated circuit element having a reflection protecting-layer between a base plate and a resist layer, the reflection protecting-layer is optionally removed by a solvent after forming a resist pattern.

As described hereinabove, solvents for cleaning or rinsing are employed for removing the resist or the reflection protecting-layer, for preventing peeling and formation of beads and, for cleaning or rinsing a coating apparatus in the lithography technology, and there have been known (the previously-described JP-A-92049938 Official Gazette, etc.) a variety of solvents composed of conventional organic solvents alone. And, it is actual circumstances that there is demanded an excellent solubility to a reflection protecting-layer or a resist and an excellent removing property in such the solvents.

Besides, an aqueous solution becomes recently often employed in the case of preparation of a reflection protecting-layer. And, for the reflection protecting-layer formed from an aqueous solution, there has been also desired a supply of a rinsing liquid which has a preferred rinsing effect such as a shortened dissolving time and, further, which also satisfies safeness to a fire and in handling.

In JP-A-05188598, JP-A-06069190, and JP-A-06148896 Official Gazettes, there is proposed a reflection protecting-layer formed from an aqueous solution. However, it has been difficult to simultaneously satisfy the demand by conventional rinsing liquids.

As described hereinabove, something of conventional solvents for resist do not show a sufficient dissolving ability to resist, and those take a long time or a large amount for sufficiently cleaning and rinsing, and something of conventional solvents have a very high toxicity, as a result, there are not solvents which simultaneously satisfy an excellent dissolving ability and safeness to human body, etc., and there have been desired the solvents which simultaneously satisfy an excellent dissolving ability and safeness to human body.

The fact is the same even in the case of the preparation of a color filter and a liquid crystal display element in addition to the preparation of an integrated circuit element.

Purpose of the present invention No. I is to provide a 3-alkoxy-1-propanol having the content of alcoholic impurities of not more than 0.3%, particularly, a high purity 3-methoxy-1-propanol, and a method for the preparation thereof.

Purpose of the present invention No. II is to provide a cleaning agent for lithography which does not have the above-described drawbacks, that is, which can be usefully employed for cleaning a coating apparatus such as an inside of a coater-cup, for removing an unnecessary resist on a base plate during or after coating a resist, for removing a resist from a base plate after having attained the purpose of the resist, and for cleaning the base plate after having removed the resist, and which also has a high dissolving ability capable of quickly cleaning in a short cleaning time of period by a small use amount, and high safeness to human body.

Purpose of the present invention No. III is to provide a rinsing liquid which does not have the above-described drawbacks, that is, which is employed for rinsing a resist formed from an organic solvent solution and a reflection protecting-layer formed from an organic solvent solution or an aqueous solution, and which has a dissolving ability and a removing ability to the resist and a reflection protecting-layer, and in which danger of fire is improved, and which is easy in handling based on Fire Defence Law in Japan, etc.

Purpose of the present inventions No. IV and V is to solve the problems in the above-described prior arts, and to provide a liquid resist composition in which a dissolving ability is improved in the preparation of the resist composition and stability is jumpingly elevated and, an amount of a residual solvent in a resist layer is decreased in the preparation of the resist layer, and there are improved properties such as the ratio of remaining solvents, uniformity of line width, and adhesion, etc. of a resist layer during development, and in which a homogeneity and delicateness are improved, and provides a solvent to be employed for the composition.

DISCLOSURE OF THE INVENTION

The present inventors, as a result of an intensive investigation, have found out that the above-described problems can be solved by the following matters, and the present invention has been completed.

In the present invention No. I, it was found out that a 3-alkoxy-1-propanol having the content of alcoholic impurities of not more than 0.3% by weight, particularly, 3-methoxy-1-propanol can be obtained through a step in which a 3-alkoxy-1-propanal is produced by allowing to react acrolein with an alcohol such as methanol using acrolein having the content of propionaldehyde of not more than 1% by weight as a raw material, a step in which the 3-alkoxy-1-propanal is hydrogenated to produce a 3-alkoxy-1-propanol in a state of residual aldehyde concentration of not more than 0.5% by weight in a crude liquid of a hydrogenation reaction, and an evaporation step of the 3-alkoxy-1-propanol, and the present invention No. I has been completed.

In the present invention No. II, there is employed a solvent (a) composed of a 1,3-propanediol alkylether, 1,3-propanediol alkylether acetate, or a mixture thereof as a cleaning agent, and the present invention No. II has been completed.

In the present invention No. III, it was found out that a dissolving ability or removing ability to a resist or a reflection protecting-layer is elevated by employing a mixture of the solvent (a) with water as a cleaning agent compared to a case composed of a water-soluble organic solvent alone, and a flash point of a mixed solvent is elevated by containing water, and danger such as fire is also reduced, that is, there is also improved safeness in handling based on Fire Defence Law, and the present invention No. III has been completed.

The present invention No. IV can be attained by employing the solvent (a) as a solvent for a resist resin, etc.

The present invention No. V can be attained by employing a resin composition composed of the solvent (a) and a specified modified copolymer as a resist composition.

The present invention 1 provides a high purity 3-alkoxy-1-propanol having the content of alcoholic impurities of not more than 0.3% by weight.

The present invention 2 provides a high purity 3-alkoxy-1-propanol as described in the present invention 1, in which the 3-alkoxy-1-propanol is 3-methoxy-1-propanol.

The present invention 3 provides a high purity 3-alkoxy-1-propanol as described in the present invention 2, in which the alcoholic impurities are 2-methyl-1-pentanol and/or methanol.

The present invention 4 provides a method for the preparation of a high purity 3-alkoxy-1-propanol characterized in that a 3-alkoxy-1-propanal is produced by allowing to react acrolein with a linear or branched alcohol having a carbon number of 1–4 using acrolein having the content of propionaldehyde of not more than 1% by weight as a raw material, a 3-alkoxy-1-propanol is produced by a hydrogenation reaction of a reaction mass using hydrogen under the presence of a catalyst, followed by recovering through a distillation the 3-alkoxy-1-propanol having the content of alcoholic impurities of not more than 0.3% by weight from a crude solution in the hydrogenation reaction.

The present invention 5 provides a method for the preparation of a high purity 3-alkoxy-1-propanol as described in the present invention 4 characterized in that the concentration of a residual aldehyde compound in the crude solution is adjusted to not more than 0.5% by weight in the hydrogenation reaction.

The present invention 6 provides a method for the preparation of a high purity 3-alkoxy-1-propanol as described in the present invention 4 or 5, in which the 3-alkoxy-1-propanol is 3-methoxy-1-propanol.

The present invention 7 provides a method for the preparation of a high purity 3-alkoxy-1-propanol as described in the present invention 6, in which the alcoholic impurities are methanol and/or 2-methyl-1-pentanol.

The present invention 8 provides a solvent for a resist which comprises a solvent (a) which is a 1,3-propanediol alkylether, 1,3-propanediol alkylether acetate, or a mixture thereof.

The present invention 9 provides a solvent for a resist as described in the present invention 8, characterized in that the content of alcoholic impurities contained in the solvent (a) is not more than 0.3% by weight.

The present invention 10 provides a solvent for a resist as described in the present invention 8 or 9, in which the alcoholic impurities are 2-methyl-1-pentanol and/or methanol.

The present invention 11 provides a cleaning agent for a lithography composed of the solvent for a resist as described in any one of the present inventions 8–10.

The present invention 12 provides a cleaning agent for lithography as described in the present invention 11, characterized in that there are further contained linear or branched alcohols (b) having a carbon number of 2–4.

The present invention 13 provides a cleaning agent for lithography as described in the present invention 12, characterized in that the alcohols (b) are ethanol, 1-propanol, 2-propanol, or a mixture thereof.

The present invention 14 provides a cleaning agent for lithography as described in any one of the present inventions 11–13, characterized by comprising a homogeneous solvent containing solvents (c) of the group A described below.

Group A
  Propylene glycol alkylether
  Propylene glycol alkylether acetate
  Ethylene glycol alkylether
  Ethylene glycol alkylether acetate
  Alkyl acetate
  Alkyl propionate
  Alkyl alkoxypropionate
  Alkyl lactate
  Aliphatic ketone
  Alkoxybutanol, or
  A mixture thereof The present invention 15 provides a cleaning agent for lithography as described in the present invention 14, characterized in that the solvents of the group A are propylene glycol methylether, propylene glycol ethylether, propylene glycol propylether, propylene glycol methylether acetate, propylene glycol ethylether acetate, propylene glycol propylether acetate, ethylene glycol ethylether acetate, n-butyl acetate, methyl methoxypropionate, ethyl ethoxypropionate, 2-heptanone, methoxy butanol, and ethyl lactate, or a mixture thereof.

The present invention 16 provides a rinsing liquid for lithography comprising the solvent for a resist as described in any one of the present inventions 8–10 and water (d).

The present invention 17 provides a rinsing liquid for lithography as described in the present invention 16, characterized in that the water (d) is an ultra-high pure water.

The present invention 18 provides a rinsing liquid for lithography as described in the present invention 16 or 17, characterized by further containing a water-soluble organic solvent (d').

The present invention 19 provides a cleaning agent for lithography as described in the present invention 18, characterized in that the water-soluble organic solvents (d') are a solvent of the group A" described below.

Group A"
  Propylene glycol alkylether
  Propylene glycol alkylether acetate
  Ethyl lactate
  Methylisobutyl ketone
  Methylethyl ketone
  Acetone, or
  A mixture thereof The present invention 20 provides a rinsing liquid for lithography as described in any one of the present inventions 16–19, in which the content of water is 0.5–200 parts by weight based on 100 parts by weight of total organic solvents.

The present invention 21 provides a rinsing liquid for lithography as described in any one of the present inventions 16–20, in which it is employed for rinsing a resist layer or a reflection protecting-layer.

The present invention 22 provides a solvent for a resist composition comprising the solvent for a resist as described in any one of the present inventions 8–10.

The present invention 23 provides a solvent for a resist composition as described in the present invention 22, characterized by further containing other solvents (c') in the group A' described below.

Group A'
  Propylene glycol alkylether
  Propylene glycol alkylether acetate
  Alkyl acetate
  Alkyl propionate
  Alkyl alkoxypropionate
  Alkyl lactate
  Aliphatic ketone, or
  A mixture thereof The present invention 24 provides a resist composition comprising a resist resin (F) and the solvent for a resist composition as described in the present invention 22 or 23.

The present invention 25 provides a photo-resist composition for a printed circuit board comprising a modified copolymer (B') and the solvent for a resist composition as described in the present invention 22 or 23.

The present invention 26 provides a photo-resist composition for a printed circuit board as described in the present invention 25, characterized in that the modified copolymer (B') is a copolymer in which an epoxy group-contained unsaturated compound (Uc) having an aliphatic structure is added to carboxylic groups in a copolymer of a copolymerizable unsaturated carboxylic acid (Ua) with an unsaturated compound (Ub) other than the unsaturated carboxylic acid.

BEST MODE FOR CARRYING OUT THE INVENTION

Figure 1:
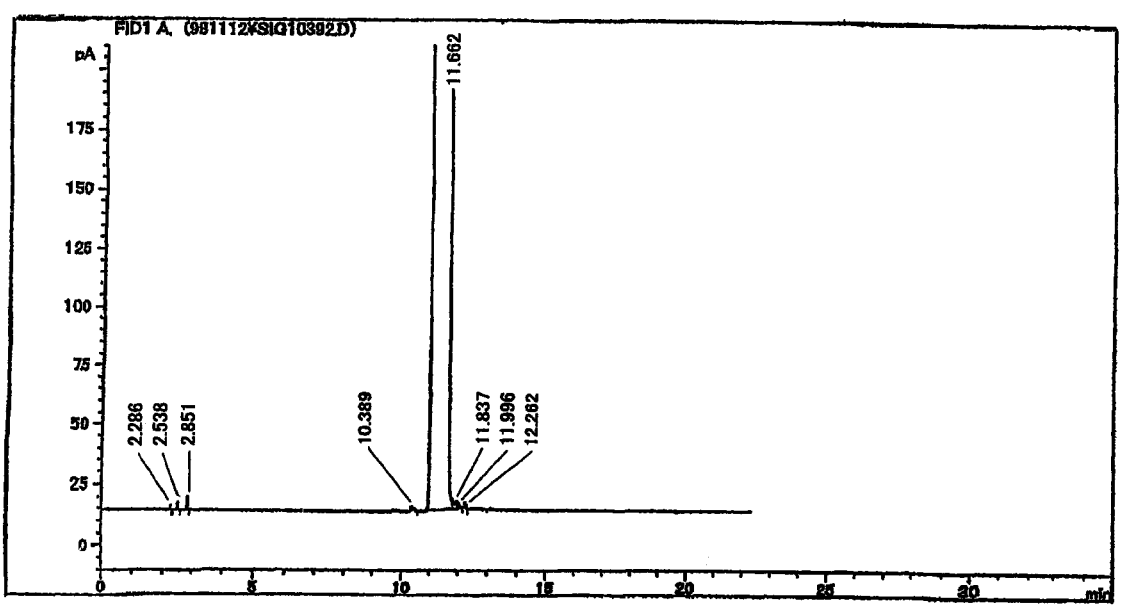
FIG. 1 is a gas chromatogram of a high purity 3-alkoxy-1-propanol in relation to the present invention. Axis of abscissas shows a retention time (minute).

Hereinafter, embodiments for carrying out the present invention are illustrated.

A 3-alkoxy-1-propanol is prepared through an addition reaction step in which a 3-alkoxy-1-propanal which is an intermediate is produced by allowing to react acrolein with a linear or branched alcohol having a carbon number of 1–4, a hydrogenation step in which 3-alkoxy-1-propanol is produced by a hydrogenation of the 3-alkoxy-1-propanal, and a distillation step in which the 3-alkoxy-1-propanol is isolated by distillation from a crude solution in the hydrogenation reaction.

As the linear or branched alcohol having a carbon number of 1–4, there are enumerated methanol, ethanol, propanol, isopropanol, butanol, isobutanol, secondary butanol, and tertiary butanol.

The alcoholic impurities mingled in the 3-alkoxy-1-propanol are an alcohol having the same alkyl group as in the alkoxy group, that is, the linear or branched alcohol having a carbon number of 1–4 which is employed as a raw material and/or an alcohol such as 2-methyl-1-pentanol derived from impurities in acrolein which is a raw material. The linear or branched alcohol having a carbon number of 1–4 is produced also from an intermediate such as a formula (vii) described hereinafter in addition to the unreacted raw material.

Hereinafter, 3-methoxy-1-propanol is illustrated as a typical example.

Reaction formulae are described below.

  (i)

  (ii)

As acrolein which is a raw material, there is employed an acrolein having the content of propionaldehyde of not more than 1.0% by weight, preferably not more than 0.3% by weight, and the content of acrylic acid of not more than 1.0% by weight, preferably not more than 0.3% by weight.

(1) Addition Reaction Step

In the addition reaction step, methanol is added to the double bond of acrolein, and 3-methoxy-1-propanal is produced which is an intermediate.

In the case of the addition reaction, a basic catalyst is employed such as potassium hydroxide and sodium hydroxide, and an aqueous solution of sodium hydroxide is preferably employed in view of costs. Concentration of the catalysts depends upon catalysts to be employed, if it is within a range in which the reaction substantially proceeds, it is not particularly limited and, for example, in the case of sodium hydroxide, it is 10–5,000 ppm by weight, and preferably 50–500 ppm by weight in the reaction system.

In the case that the concentration of the catalysts is too small, an effect is not sufficiently obtained and, in the case that it is too much, impurities unpreferably increase by condensation reaction of the 3-alkoxy-1-propanal which is an intermediate.

Further, molar ratio of methanol with respect to acrolein is 2–20, and preferably 5–15. In the case that the molar ratio is less than 2, a polymerization reaction of acrolein itself is apt to be caused and, in the case of exceeding 20, the reaction rate unpreferably lowers, and costs for recovery of methanol unpreferably increase.

Reaction temperature is not particularly limited, if it is within a range in which the reaction substantially proceeds and, for example, it is −10–30° C., and preferably −5–10° C. In the case that the reaction temperature is too low, the reaction rate unpreferably lowers and, in the case that the reaction temperature is too high, selectivity in the reaction unpreferably lowers.

Reaction style in the addition reaction may be any of a continuous, semi-batch, and batch style.

As a reaction apparatus, there can be employed a mixable vessel and a tubular type reaction vessel, etc.

(2) Hydrogenation Step

In the hydrogenation (also referred to as an addition of hydrogen) step, the aldehyde group in 3-methoxy-1-propanal which is an intermediate is hydrogenated to produce 3-methoxy-1-propanol which is a desired product.

In the hydrogenation of 3-methoxy-1-propanal, there are employed a catalyst for hydrogenation such as a metal catalyst which includes platinum, palladium, and nickel, and a catalyst in which the metal is carried on a carrier such as carbon and alumina, etc., and a Raney's nickel is preferably employed from a viewpoint of costs.

Reaction temperature for the hydrogenation is not particularly limited, if it is within a range in which the reaction substantially proceeds and, for example, it is 100–200° C., and preferably 130–150° C. In the case that the reaction temperature in the hydrogenation is too low, the reaction for hydrogenation does not unpreferably proceed and, in the case that it is too high, a decomposition reaction of methanol is unpreferably caused.

Partial pressure of hydrogen in the reaction system is not particularly limited, if it is within a range in which the reaction substantially proceeds and, for example, it is 5–20 MPa, and preferably 10–15 MPa. In the case that the partial pressure of hydrogen is too low, the hydrogenation does not sufficiently proceed and, in the case that it is too high, although being not problematic in the reaction, plant costs unpreferably increase.

Reaction style in the hydrogenation reaction may be any of a continuous, semi-batch, and batch style.

As a reaction apparatus, there can be employed a mixable vessel and a tubular type reaction vessel, etc.

In order that hydrogen is sufficiently supplied, agitation, mixing, and dispersion, etc. are conducted.

Further, in the case that an aldehyde compound is remained in the reaction crude liquid after the hydrogenation step, decomposition reaction is caused in the distillation step, and alcoholic impurities such as methanol are produced, resulting in that those mingle in the target product 3-methoxy-1-propanol which is a distillate. For that reason, it is important that concentration of the aldehyde compounds remained is adjusted to not more than 0.5% by weight, and preferably not more than 0.1% by weight in the reaction crude liquid after the hydrogenation step.

By-products (Influence of Propionaldehyde)

In the present invention, in the case that propionaldehyde is contained as an impurity in acrolein which is a raw material, 2-methyl-1-pentanol which is a by-product is produced according to formulae (iii) and (iv) described below.

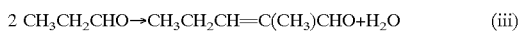  (iii)

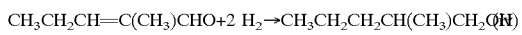  (iv)

It is to be noted that it is thought that dehydration is caused after through an aldol condensation of propion aldehyde in the formula (iii).

(Influence of Acrylic Acid)

In the case that acrylic acid is contained as an impurity in acrolein which is a raw material, there are produced acrylic acid which is a by-product and 3-methoxy-1-methylpropionate in which methanol is added to acrylic acid according to formulae (v) and (vi) described below.

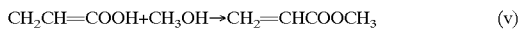  (v)

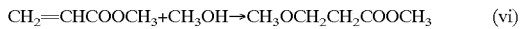  (vi)

(Influence of Ethanol)

In the case that ethanol mingles in the reaction system, it reacts with acrolein, followed by producing 3-ethoxy-1-propanol through hydrogenation.

Ethanol is produced by hydrogenation of acetaldehyde contained in acrolein which is a raw material or acetic acid derived from a catalyst.

(Influence of Croton Aldehyde)

In the case that croton aldehyde mingles in the reaction system, croton aldehyde reacts with methanol, followed by producing 3-methoxy-1-butanol by hydrogenation.

It is to be noted that croton aldehyde is produced by an aldol condensation of acetaldehyde contained in acrolein which is a raw material.

(Influence of 3-methoxy-1-propanal)

As other by-product, 1,1,3-trimethoxypropane (that is, 3-methoxy-1-propanal dimethylacetal) is found out which is produced by a reaction of 3-methoxy-1-propanal which is an intermediate with methanol.

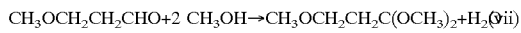

By the presence of 1,1,3-trimethoxypropane, there is caused decomposition to 3-methoxy-1-propanal which is an intermediate and methanol by heating under of water.

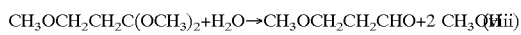

Accordingly, it is preferred that hydrogenation ratio of 3-methoxy-1-propanal is higher, the residual concentration in the reaction crude liquid after the hydrogenation step is adjusted to not more than 0.5% by weight, and preferably not more than 0.1% by weight.

Although the above-described impurities are different depending upon the kind, since the impurities affect to synthesis of a derivative and use as a functional solvent, particularly, it is required that the content of the alcoholic impurities is reduced to not more than a determined amount.

In 3-methoxy-1-propanol which is a target product and 2-methyl-1-pentanol which is a by-product, standard boiling point is 153° C. and 150° C., respectively, those are very close to each other, and it is difficult to be separate by a usual distillation and, even though those are separated from each other, since it is required to increase separation stages of a distillation column and largely elevate ref lux ratio, it is disadvantageous because of an increase of plant costs and large energy consumption. Accordingly, it is important that there is employed acrolein having the propionaldehyde content of not more than 1% by weight as a raw material. In the case that the propionaldehyde content exceeds 1% by weight, as described hereinabove, it is difficult to separate by distillation, resulting in that the 2-methyl-1-pentanol content cannot be reduced to not more than 0.3% by weight in 3-methoxy-1-propanol.

(3) Distillation Step

In the distillation step, 3-methoxy-1-propanol which is the target product is isolated and recovered from the reaction crude liquid after the hydrogenation reaction.

The distillation step is conducted by a distillation treatment composed of recovery of methanol by distillation from the reaction crude liquid in the hydrogenation reaction, distilling off of low boiling ingredients from a residual liquid after recovery of methanol, recovery of 3-methoxy-1-propanol which is the target product by refining distillation, and discharge of residual substances having high boiling points.

Distilling operation may be conducted by any of a continuous distillation, semi-batch distillation, and batch distillation.

Distilling conditions of 3-methoxy-1-propanol are preferred in the stage number of 10–50 in distillation column, reflux ratio of 1–10, bottom liquid temperature of 80–120° C., and column top pressure of 5–50 torr.

<1,3-propanediol Derivative-based Solvent>

As the 1,3-propanediol derivative-based solvent, there are enumerated a 1,3-propanediol alkylether, a 1,3-propanediol alkylether acetate, a 1,3-propanediol dialkylether, and a 1,3-propanediol diacetate.

1,3-propanediol alkylether acetate, etc. is obtained using the 3-alkoxy-1-propanol (that is, a 1,3-propanediol alkylether).

Particularly, a high purity 1,3-propanediol methylether acetate can be prepared using a high purity 3-methoxy-1-propanol.

By the present invention, the 1,3-propanediol derivative-based solvent, particularly, a 1,3-propanediol alkylether and a 1,3-propanediol alkylether acetate, etc. are obtained in a high purity. For example, in a high purity 3-methoxy-1-propanol, total content of the alcoholic impurities (2-methyl-1-pentanol, methanol, or a mixture thereof, particularly, methanol and 2-methyl-1-pentanol which affect in various cases) can be reduced to not more than 0.3% by weight, and preferably, not more than 0.1% by weight.

[1] Relating to a Solvent for Resist

As solvents to be employed in the present inventions Nos. II–V, there are enumerated at least one kind of solvents selected from the group consisting of the 1,3-propanediol alkylether, the 1,3-propanediol alkylether acetate, the 1,3-propanediol dialkylether, and the 1,3-propanediol diacetate.

In the alkylether, an alkyl group is, if it can attain the purpose of the present invention, not particularly limited and, preferably, it is a linear or branched alkyl group having a carbon number of 1–4.

As the 1,3-propanediol alkylether, there are enumerated 1,3-propanediol methylether, 1,3-propanediol ethylether, 1,3-propanediol-1-propylether, 1,3-propanediol-2-propylether, 1,3-propanediol-n-butylether, 1,3-propanediol-iso-butylether, and 1,3-propanediol-t-butylether, etc. These may be even a mixture of two or more kinds.

As the 1,3-propanediol alkyletheracetate, there are enumerated 1,3-propanediol methylether acetate, 1,3-propanediol ethylether acetate, 1,3-propanediol-1-propylether acetate, 1,3-propanediol-2-propylether acetate, 1,3-propanediol-n-butylether acetate, 1,3-propanediol-iso-butylether acetate, and 1,3-propanediol-t-butylether acetate, etc. These may be even a mixture of two or more kinds.

As the 1,3-propanediol dialkylether, there are enumerated dialkylethers corresponding to the 1,3-propanediol alkylether and, further, there are exemplified ones having different combination of the alkyl group in the dialkylethers.

The above-described solvents are exceedingly high in safeness and solubility.

<Solvent (a)>

In the above-described solvents, as solvents to be employed in the present inventions Nos. II–V, there are enumerated preferably the 1,3-propanediol alkylether, the 1,3-propanediol alkylether acetate, or a mixture thereof, and these are named the solvent (a) (herein, the alkylether group is a linear or branched one having a carbon number of 1–4).

The solvent (a) can be employed solely and also in any mixing ratio of two or more kinds.

As a mixture of two or more kinds, for example, there are enumerated a mixture of 1,3-propanediol methylether with 1,3-propanediol methylether acetate and a mixture of 1,3-propanediol ethylether with 1,3-propanediol methylether acetate.

Further, the solvent (a) can be employed solely and also in any mixing ratio with a solvent in solvents (c) of an A group described hereinafter. For example, there are preferably enumerated a mixture of 1,3-propanediol methylether with propylene glycol monomethylether acetate, a mixture of 1,3-propanediol ethylether with propylene glycol monomethylether acetate, a mixture of propylene glycol methylether with 1,3-propanediol methylether acetate, and a mixture of propylene glycol ethylether with 1,3-propanediol methylether acetate, etc.

As a mixture of two or more kinds, of the above mixtures, there is particularly preferred an alkylether and/or an alkylether acetate of 1,3-propanediol and, specifically, there is exemplified the combination of a methylether with methylether acetate of 1,3-propanediol.

It is to be noted that the above-described solvents (a) in the present invention are employed as a homogeneous solution by mixing with various solvents and water described hereinafter, and the homogeneous solution, in addition to a case of a solution in which the respective solvents and water preferably dissolve each other in use conditions, means also a case of a state in which a component disperses in other components if it does not form a separated layer.

Further, in the case that various solvents are mixed with the above-described solvents (a), the various solvents are selected within a range in which those do not affect to homogeneity and delicateness of a dried resist coating layer by remarkable evaporation of the various solvents or remaining in the resist.

Still further, there are preferably employed the various solvents having a lower boiling point than a boiling point of the solvents (a).

Hereinafter, characteristic matters are illustrated in relation to solvents in the present invention No. II.

The cleaning agent for lithography of the present invention may be even the solvent (a) alone, and even a homogeneous solvent which is a mixture with alcohols (b) and/or solvents (c) in the group A described hereinafter.

<Alcohols (b)>

As the alcohols (b) which have a linear or branched chain having a carbon number of 1–4, there are enumerated ethanol, 1-propanol, 2-propanol, 1-butanol, 2-butanol, sec-butanol, t-butanol, and a mixture thereof, there are preferred ethanol, 1-propanol, 2-propanol, and a mixture thereof.

As examples employed in combination with two or more kinds of alcohols, for example, there are enumerated a combination of ethanol with 1-propanol and a combination of ethanol with 2-propanol.

It goes without saying that the alcohols to be employed in the present invention are not limited to ones specifically exemplified.

<Solvents (c) in the Group A>

As the solvents (c) in the group A, there are enumerated a propylene glycol alkylether, a propylene glycol alkylether acetate, an ethylene glycol alkylether, an ethylene glycol alkylether acetate, an alkyl acetate, an alkyl propionate, an alkyl alkoxypropionate, an alkyl lactate, an aliphatic ketone, an alkoxybutanol, and a mixture thereof. The solvents (c) in the group A can be employed also in combination of two or more kinds. It is to be noted that in the case that an ethylene glycol-based solvent becomes problematic in harmfulness, it may be even not employed.

The alkyl group in the above-described alkylethers, if it can attain the purpose of the invention, is not particularly limited and, for example, it is a linear or branched alkyl group having a carbon number of 1–4.

As the preferred solvents (c), there are preferably enumerated (1) the propylene glycol alkylether which includes propylene glycol monomethylether, propylene glycol monoethylether, propylene glycol monopropylether, and propylene glycol mono-n-butylether, etc., (2) the propylene glycol alkylether acetate includes propylene glycol monomethylether acetate and propylene glycol monoethylether acetate, etc., (3) the ethylene glycol alkylether includes ethylene glycol monomethylether, ethylene glycol monoethylether, and ethylene glycol monopropylether, (4) the ethylene glycol alkylether acetate includes ethylene glycol monomethylether acetate and ethylene glycol monoethylether acetate, (5) the alkyl acetate includes propyl acetate, n-butyl acetate, and n-amyl acetate, etc., (6) the alkyl propionate includes methyl propionate, ethyl propionate, and butyl propionate, etc., (7) the alkyl alkoxypropionate includes methylmethoxy propionate, ethylmethoxy propionate, ethylmethoxy propionate, and methylethoxy propionate, (8) the alkyl lactate includes methyl acetate and ethyl acetate, etc., (9) the aliphatic ketone includes 2-butanone, 2-pentanone, 2-hexanone, and 2-heptanone, etc., (10) the alkoxybutanol includes methoxybutanol and ethoxybutanol, etc.

Of those, there are preferably propylene glycol monomethylether, propylene glycol monoethylether, propylene glycol monopropylether, propylene glycol monomethylether acetate and propylene glycol monoethylether acetate, ethylene glycol monoethylether acetate, n-butyl acetate, methyl methoxypropionate, methyl ethoxypropionate, ethyl lactate, 2-heptanone, and methoxybutanol.

It goes without saying that the organic solvent of the group A to be employed in the present invention are not limited to ones specifically exemplified.

21 Mixing Ratio of Respective Solvents as the Cleaning Agent for Lithography>

The mixing ratio of the solvent (c) of the group A with the solvent (a) and the alcohols (b) depends upon the kind thereof and, usually, mixing weight ratio (hereinafter, the same) of the solvent (a): the alcohols (b): the solvent (c) of the group A is 10–100:0–80:0–80, preferably 40–90:5–60:5–60, and more preferably 60–80:10–40:10–40.

Hereinafter, characteristic matters are illustrated in relation to solvents in the present invention No. III.

The rinsing liquid for lithography of the present invention is a homogeneous solution composed of the above-described solvent (a) and water (d).

Further, the rinsing liquid for lithography of the present invention may be even composed of the above-described solvent (a) and water (d), and further, other water-soluble organic solvent (e).

As the water (d), there are enumerated an ion-exchanged water, distilled water, and ultrafiltration-treated water, etc. and, preferably, ultra high pure water obtained in combination thereof.

The ultra high pure water is a water having resistivity value of approximately $10 \times 10^4 – 1800 \times 10^4$.

<Water-soluble Organic Solvent (e)>

The water-soluble organic solvent (e) has been conventionally employed as a solvent or a rinsing liquid for resist or a reflection protecting layer, and there can be employed even any of water-soluble organic solvents.

The water-soluble organic solvent (e) is, specifically, a solvent in the group A" described below.

Group A": propylene glycol alkylether, propylene glycol alkylether acetate, ethyl lactate (EL), methyl isobutyl ketone, methyl ethyl ketone, acetone, or a mixture thereof.

The alkyl group in the above-described alkylethers, if it can attain the purpose of the invention, is not particularly limited and, for example, it is a linear or branched alkyl group having a carbon number of 1–4.

As the propylene glycol alkylether, there are included propylene glycol methylether, propylene glycol ethylether, and propylene glycol propylether, etc., and as the propylene glycol alkylether acetate, there are included propylene glycol methylether acetate and propylene glycol ethylether acetate, and propylene glycol propylether acetate, etc.

Preferred water content in the rinsing liquid cannot be simply decided because it depends upon the solvent to be employed and, it is usually 0.5–200 parts by weight, and preferably 0.5–100 parts by weight based on 100 parts by weight of total organic solvents which are the sum of the organic solvent (a) and the water-soluble organic solvent (e) which is optionally added.

Use of Solvents for Lithography of the Present Invention Nos. II and III

Hereinafter, solvents to be employed as the cleaning agent for lithography and the rinsing liquid for lithography are collectively named the solvents for lithography.

The solvents for lithography can be applied for a publicly-known positive type resist, negative type resist, and reflection protecting-layer.

A resist material composed of a quinone diazide-based photosensitive agent and an alkali-soluble resin is preferred in application for the solvent for lithography of the present invention.

Further, a chemical amplification type resist is also preferred in application for the solvent for lithography of the present invention.

The solvent for lithography of the present invention can be partially applied as a cleaning agent for a publicly-known reflection protecting-layer in which an organic solvent-based cleaning agent is employed, and which is coated for suppressing generation of an interference wave in a resist layer.

Application of the solvent for lithography of the present invention is further specifically illustrated.

For example, in the case that coating of the resist composition is conducted by a spin-coating method, although there is a tendency that beads of the resist or reflection protecting-layer are formed along an edge of a base plate, a resist layer or reflection protecting-layer having substantially uniform thickness can be formed on the base plate by spraying the solvent for lithography of the present invention onto rotating beads at the edge, whereby, accelerating a flow of the beads. Further, the resist or reflection protecting-layer moved toward the periphery of side surface or back surface in the base plate can be removed by spraying the solvent for lithography of the present invention.

Since the rinsing liquid for lithography of the present invention contains water, it has a good affinity (contact angle is small) to a layer formed from an aqueous solution, and an excellent rinsing effect is also obtained for a reflection protecting-layer formed from an aqueous solution.

Further, in the case that a reflection protecting-layer is formed between a base plate and a resist layer, for example, in a positive type resist, a reflection protecting-layer not having a resist layer is wetted and removed using the rinsing liquid after formation of a pattern by exposing to light and developing.

Coating of the resist or reflection protecting-layer is conducted using a coating apparatus, and the coating apparatus is occasionally employed again as a coating apparatus for another materials after coating of the resist or reflection protecting-layer onto a base plate. For example, it is occasionally employed as a coating apparatus for a reflection protecting-layer from a resist, a different kind of a resist from the resist, and a resist from a reflection protecting-layer. In such the case, a coating apparatus is washed before employing as the coating apparatus for different kind of materials. Also in such the case, the solvents of the present invention can be effectively utilized as a rinsing liquid.

After formation of a resist pattern, there is conducted a determined treatment such as etching, plating, and ion-diffusion for forming a circuit element utilizing the resist pattern, and the resist pattern is removed using the solvent of the present invention as a cleaning agent.

After removal, rinse is optionally further conducted by the cleaning agent and the rinsing liquid of the present invention.

Further, in the case that a solvent for removal is water-insoluble or an amine-based organic solvent differently from the cleaning agent of the present invention, a rinse can be also conducted by a pure water after having optionally rinsed by cleaning agent of the present invention. Still further, the solvent for lithography of the present invention can be effectively utilized for cleaning or rinsing a coating apparatus.

Hereinafter, characteristic matters are illustrated in relation to the solvents in the present invention No. IV.

<Solvent (A) for a Resist>

In the present invention No. IV, the solvent (A) for a resist composition is composed of the above-described solvent (a) The solvent (A) for a resist composition may be the solvent (a) alone or even a mixture of the solvent (a) with other solvents (c')

In the solvent (a), it is preferred that content of the impurities, particularly, alcoholic impurities is low, for example, it is not more than 0.3% by weight, and preferably not more than 0.1% by weight. In the case that a large amount of the alcoholic impurities are contained in the solvent (A), a homogeneous coating layer having a constant quality is occasionally apt to be not obtained because evaporation order of the solvents is different from each other.

As the alcoholic impurities, there are enumerated methanol and 2-methyl-1-pentanol, etc. For example, in the case of containing an alcohol having a low boiling point, the homogeneous coating layer is apt to be not obtained because of accelerated drying at surface. Further, in the case that the alcohol having a low boiling point is methanol, it is a poisonous substance and, for that reason, working circumstance must be severely controlled. Still further, methanol is apt to exhibit a corrosive property for a copper thin layer to be employed in a resist. On the other hand, an alcohol having a high boiling is apt to be left on a coating layer even though being baked. Accordingly, a delicate resist layer is apt to be not obtained.

<Solvent (c')>

The solvent for a resist composition of the present invention No. IV may be even composed of a mixed solvent of the above-described solvent (a) with other solvents (c').

As the other solvents (c'), the group A' described below is enumerated.

As the group A', there are enumerated the propylene glycol alkylether acetate, the propylene glycol alkylether, the alkyl lactate, the alkyl acetate, the alkyl propionate, the alkyl alkoxypropionate, and the aliphatic ketone.

(1) As the propylene glycol alkylether acetate, there are exemplified propylene glycol monomethylether acetate and propylene glycol monoethylether acetate, propylene glycol monopropylether acetate, and propylene glycol monobutylether acetate, etc.

(2) As the propylene glycol alkylether, there are exemplified propylene glycol monomethylether, propylene glycol monoethylether, and propylene glycol monopropylether, and propylene glycol monobutylether, etc.

(3) As the alkyl lactate, there are exemplified methyl lactate and ethyl lactate, etc.

(4) As the alkyl acetate, there are exemplified propyl acetate, n-butyl acetate, and n-amyl acetate, etc.

(5) As the alkyl propionate, there are exemplified methyl propionate, ethyl propionate, propyl propionate, and butyl propionate (PnB), etc.

(6) As the alkyl alkoxypropionate, there are exemplified methyl methoxypropionate, ethyl ethoxypropionate, ethyl methoxypropionate, and methyl ethoxypropionate, etc.

(7) As the aliphatic ketone, there are exemplified 2-butanone, 2-pentanone, 2-hexanone, and 2-heptanone, etc.

These may be even a mixed solvent composed of two or more kinds.

As mixing proportion of the solvent (a) with other solvents (c'), the content of the solvent (a) ranges in 10–100% by weight in the mixed solvent. The mixing proportion depends upon the solvents to be selected, for example, in the case of 1,3-propanediol methylether and 1,3-propanediol methylether acetate, it is preferably 50–100% by weight, and more preferably 50–90% by weight.

[2] In relation to a resin for a resist, etc.

<Resist Component (B)>

The resist component (B) in the resist composition (F) of the present invention No. IV may be even any of a conventionally well known or publicly-known positive type one or negative type one.

Hereinafter, there are exemplified typical resists to be employed in the present invention. As the positive type one, for example, there are enumerated a resist composed of a quinone diazide-based photo-sensitive agent and an alkali-developable resin and a chemically-amplified type positive resist, etc. As the negative type one, there are enumerated a resist containing a polymer compound having a photosensitive group such as a vinyl polycinnamate, a resist containing an aromatic azide compound, or a resist composed of a cyclized rubber and a compound containing an azide compound which is a bisazide compound, a resist containing a diazo resin, a photopolymerizable composition containing an addition-polymerizable unsaturated compound, and a chemically-amplified type negative resist composed of an alkali-soluble resin, a cross-linking agent, and an acid-producing agent, etc.

2.1 Positive Type Resist Composed of a Quinone Diazide-based Photo-sensitive Agent and an Alkali-developable Resin Preferred resist component (B) is a positive type resist composed of a quinone diazide-based photo-sensitive agent and an alkali-developable resin. Various positive type resists have been conventionally known, and any of those can be employed without any particular limitation.

<Quinone Diazide-based Photo-sensitive Agent>

As the quinone diazide-based photo-sensitive agent, there are enumerated 1,2-benzoquinone diazide-4-sulfonic acid, 1,2-naphthoquinone diazide-4-sulfonic acid, and 1,2-naphthoquinone diazide-5-sulfonic acid, an ester or amide of the sulfonic acids, etc.

The ester or amide of the sulfonic acids is obtained by a condensation reaction of a corresponding quinone diazide sulfonic acid or quinone diazide sulfonyl chloride with a compound having hydroxyl group or a compound having amino group.

As the compound having hydroxyl group, there are enumerated dihydroxy benzophenone, trihydroxy benzophenone, tetrahydroxy benzophenone, phenol, naphthol, p-methoxy phenol, bisphenol A, pyrocatechol, pyrogallol, pyrogallol methylether, gallic acid, and $\alpha,\alpha',\alpha''$-tris(4-hydroxyphenyl)-1,3,5-triisopropyl benzene, and tris (hydroxyphenyl)methane, etc. and, as the compound having amino group, there are enumerated aniline and p-aminodiphenylamine, etc.

The quinone diazide-based photo-sensitive agents can be employed solely or as a mixture of two or more kinds.

<Alkali-soluble Resin>

On the other hand, as the alkali-soluble resin, for example, there are enumerated a novolak resin, a polyvinyl phenol, a polyvinyl alcohol, and a copolymer of acrylic acid or methacrylic acid, etc.

As the novolak resin, for example, there is enumerated a condensation-polymerization product of one or more kinds of phenols such as phenol, o-cresol, m-cresol, p-cresol, xylenol, trimethyl phenol, t-butylphenol, ethylphenol, 2-naphthol, 1,3-dihydroxy naphthalene with aldehydes such as formaldehyde and paraformaldehyde.

The alkali-soluble resins such as the novolak resin can be optionally employed in combination of two or more kinds, and other resins can be also added in order to improve a thin layer-formability, etc. Further, as the quinone diazide sulphonate, there can be also employed an ester of the condensation-polymerization product of phenols with aldehydes or ketones with quinone diazide sulfonic acid.

Use proportion of the quinone diazide-based photo-sensitive agent with respect to the alkali-soluble resins depends upon a photo-sensitive agent and the alkali-soluble resins to be specifically employed and, usually, it is preferably a range of 1:1–1:20 by weight ratio. However, the present invention is not limited thereto.

2.2 Chemical Amplification-type Resist

As the resist component (B), the chemical amplification type resist is also preferably employed. In the chemical amplification type resist, a pattern is formed through producing an acid by irradiation of radiation rays such as an ultraviolet ray, a far ultraviolet ray, an X-ray, and an electron beam, etc., and by changing solubility of a portion to be irradiated by a chemical change to a developer due to a catalytic effect by the acid.

The chemical amplification-type positive resist contains, for example, a compound which produces an acid by irradiation of radiation rays and a resin containing acid-sensitive groups in which an alkali-soluble group is produced such as phenolic hydroxyl group or carboxylic group, which is decomposed under the presence of an acid.

Further, as the chemical amplification-type resist, in addition to the above-described ones, there have been known resists containing a compound which lowers an effect for suppressing the solubility of the alkali-soluble resins or accelerates the solubility of the alkali-soluble resins, which are decomposed under the presence of the alkali-soluble resins, an acid-producing agent, and an acid, and such the resists can be also employed.

<Compound which Produces an Acid>

As the compound which produces an acid by irradiation of the above-described radiation rays, there are enumerated bis sulfonyl diazomethanes such as bis(isopropylsulfonyl)

diazomethane, bis sulfonyl methanes such as methylsulfonyl-p-toluenesulfonyl methane, sulfonylcarbonyl diazomethanes such as cyclohexyl sulfonyl cyclohexylcarbonyl diazomethane, sulfonylcarbonyl alkanes such as 2-methyl-2-(4-methylphenylsulfonyl)propiophenone, nitrobenzyl sulphonates such as 2-nitrobenzyl-p-toluene sulphonate, alkyl or aryl sulphonates such as pyrogallol trismethane sulphonate, benzoin sulphonates such as benzoin tocirate, N-sulfonyloxyimides such as N-(trifluoromethyl sulfonyloxy)phthalic imide, pyrolidones such as (4-fluoro-benzenesulfonyloxy)-3,4,6-trimethyl-2-pyrolidone, sulfonates such as 2,2,2-trifluoro-1-trifluoromethyl-1-(3-vinylphenyl)-ethyl-4-chlorobenzene sulphonate, and onium salts such as triphenyl sulfonium methanesulfonate, and the compounds can be employed solely or as a mixture of two or more kinds.

<Resin Containing Acid-sensitive Groups>

Further, the resin containing acid-sensitive groups in which an alkali-soluble group is produced such as phenolic hydroxyl group or carboxylic group is comprised an acid-sensitive group which is decomposed under the presence of an acid and an alkali-soluble portion. As the acid-sensitive group, there are enumerated a substituted methyl group such as benzyl group, a 1-substituted ethyl group such as 1-methoxyethyl group and 1-benzyloxyethyl group, a 1-branched alkyl group such as t-butyl group, a silyl group such as trimethylsilyl group, a gelmyl group such as trimethygelmyl group, an alkoxycarbonyl group such as t-butoxycarbonyl group, an acyl group such as acetyl group, a cyclic acid-decomposable group such as tetrahydropyranyl group, tetrahydrophranyl group, tetrahydrothiopyranyl group, and tetrahydrothiophranyl group, etc. Of the acid-decomposable groups, there are preferably benzyl group, t-butyl group, t-butoxycarbonyl group, tetrahydropyranyl group, and tetrahydrothiophranyl group, etc.

Still further, as the alkali-soluble resin having an alkali-soluble group such as phenolic hydroxyl group or carboxylic group, for example, there are enumerated a polymer or copolymer from a vinyl monomer such as hydroxy styrene, hydroxy-α-methyl styrene, hydroxymethyl styrene, a hydroxyadamantyl(meth)acrylate, vinyl benzoic acid, carboxymethyl styrene, carboxymethoxy styrene, acrylic acid, methacrylic acid, crotonic acid, maleic acid, itaconic acid, citraconic acid, mesaconic acid, and cinnamic acid, etc., a copolymer of at least one kind of the vinyl monomers with other monomers, and a condensation-polymerization resin such as a novolak resin.

[3] In Relation to a Resist Composition

The resist composition (F) of the present invention No. IV is comprised the above-described solvent (A) for a resist and the above-described component (B). In the resist composition (F), there can be appropriately mixed a variety of additives such as a surface active agent and a sensitivity agent which are conventional publicly-known according to the purposes for use.

Use amount of the solvent (A) with respect to the resist component (B) depends upon a kind of a resist to be employed and a main solvent to be employed, and it is usually 50–3,000 parts by weight, preferably 70–2,000 parts by weight, and more preferably 100–1,000 parts by weight based on 100 parts by weight of a solid component of the resist component (B).

<Formation of a Resist Pattern>

Formation of a resist pattern using the resist composition (F) of the present invention is conducted, for example, as follows.

First of all, the resist composition (F) is prepared by dissolving the resist component (B) into the above-described solvent (A) and, undissolved components are optionally removed by a filter filtration.

A filtrate obtained is coated by a conventionally publicly-known coating method such as spin-coating, roll-coating, reverse roll-coating, cast-coating, and doctor-coating on a base plate, so that layer thickness after prebaking is adjusted to, for example, 0.01–1,000 μm. Before coating of a resist or onto a resist layer prepared by coating, a reflection protecting-layer is optionally prepared by coating.

As the reflection protecting-layer, for example, there are enumerated a polyamine acid or a polybutene acid (U.S. Pat. No. 4,910,122) to which a dye is added, a copolymer (For example, JP-A-06118656, etc.) to which a dye is added, a product (U.S. Pat. No. 2,751,373, U.S. Pat. No. 2,811,509, U.S. Pat. No. 3,763,086, U.S. Pat. No. 3,854,946, and U.S. Pat. No. 4,609,614) in which dyes,etc. are grafted on a maleic anhydride polymer, an itaconic anhydride polymer, and a polyacrylate or a polymethacrylate, a reaction product (U.S. Pat. No. 5,294,680) with a polymer having an amino aromatic chromophoric group and an anhydride group, a product (JP-A-05188598) composed of a water-soluble polymer and water soluble perfluorocarboxylic acid, an organic alkali solution (JP-A-06069120) such as tetramethylammonium hydroxide containing a water-soluble polymer, etc., a product (JP-A-06148896) composed of a water-soluble layer-formable component and a fluorine-based surface active agent, a product (JP-A-07131096) composed of a perfluoroalkyl carboxylic acid, an organic amine, and polyvinyl pyrolidone, and a product (JP-A-08129056) composed of an organic amine, polyvinyl pyrolidone, and a water-soluble alkyl siloxane polymer, and a product formed from an organic solvent or an aqueous solution.

The resist composition coated on a base plate is exposed to light and, for example, it is prebaked by a hot-plate to remove solvents and form a resist layer. Temperature for prebaking depends upon a kind of a solvent or resist to be employed, and it is usually 30–200° C., and preferably 50–150° C. or so.

After formation of the resist layer, exposure is conducted, and since a photo-sensitive region is different depending upon resists to be employed, exposure is conducted using an exposing light source corresponding to the photo-sensitive region. In the exposure, for example, there are employed publicly-known irradiation apparatuses such as a high pressure mercury lamp, a metal halide lamp, a ultra high pressure mercury lamp, a KrF eximer laser, an ArF eximer laser, an F2 laser, a soft X-ray irradiation apparatus, and an electron beam imaging apparatus and, optionally through a mask, irradiation by a fixed pattern is conducted by an ultraviolet ray, a far ultraviolet ray, an X-ray, and an electron beam, etc.

After having been exposed, development is conducted after an after-baking is optionally conducted in order to improve developability, dissolution, and a pattern shape, etc. Further, a dry-etching by a gas-plasma, etc. is optionally conducted in order to remove a reflection protecting-layer after development to form a resist pattern.

The above-described development of a resist is usually conducted using a developer and utilizing a difference of solubility to a solvent in an exposed region from an unexposed region or a difference of solubility to an alkali solution.

As an alkali developer, there are employed an aqueous solution or a water-based solution in which there are dissolved inorganic alkalis such as sodium hydroxide, potassium hydroxide, sodium carbonate, and sodium silicate, amines such as ammonia, ethylamine, diethyl amine, triethyl amine, diethylethanol amine, triethanol amine, and benzyl amine, amides such as a formamide, quaternary ammonium salts such as tetramethylammonium hydroxide (TMAH), tetraethyl ammonium hydroxide, and a choline, cyclic amines such as pyrrole and piperazine.

From the resist coated on a base plate, solvents are removed by baking to prepare a resist layer having the thickness of usually 0.4–2.5 μm, if a reflection protecting-layer is formed, 1–2.5 μm or so.

<Uses of a Resist Composition (F)>

The resist composition (F) of the present invention can be employed in a variety of uses such as the preparation of a semiconductor device or the preparation of a liquid crystal display element, and it is preferably employed as a photoresist composition for the preparation of a semiconductor or the preparation of a liquid crystal display element.

Hereinafter, characteristic matters are illustrated in the present invention No. V.

In the photoresist resin composition (F') for a printed circuit board of the present invention, the specified modified copolymer (B') is employed as a resin component in the above-described resist composition (F), and it is comprised the above-described solvent (A) and the specified modified copolymer (B').

However, in the present invention No. V, the above-described solvent (a) is a main solvent in the solvent (A).

Further, the solvent (A) may also be comprised a mixed solvent of the main solvent (a) with the above-described other solvent (c').

Of the other solvent (c'), propylene glycol monomethylether acetate and propylene glycol monomethylether, etc. are more preferred from a viewpoint of miscibility with the modified copolymer (B').

It is to be noted that even though the case of a mixed solvent with main solvents themselves or the other solvent (c'), in order to improve homogeneity and delicateness of a coating layer, the content of the alcoholic impurities is preferred in the above-described range.

The content of the main solvent (a) in the solvent (A) is preferably not less than 50% by weight, and more preferably 80–100% by weight (total amount of the main solvent and solvent to be employed together is 100% by weight).

A range to be applied depends upon the main solvent to be selected and, for example, in the case of 1,3-propanediol methylether and 1,3-propanediol methyletheracetate, it is preferably 50–100% by weight, and more preferably 50–90% by weight.

<Modified Copolymer (B')>

A preferred modified copolymer (B') to be employed in the present invention is the modified copolymer (B') in which an epoxy group-contained unsaturated compound (Uc) having a cycloaliphatic structure is added to carboxylic groups in a copolymer of a copolymerizable unsaturated carboxylic acid (Ua) with an unsaturated compound (Ub) other than the unsaturated carboxylic acid.

<Unsaturated Carboxylic Acid (Ua)>

The copolymerizable unsaturated carboxylic acid (Ua) to be employed in the modified copolymer (B') can be copolymerized with the "unsaturated compound (Ub) other than the unsaturated carboxylic acid" and, it is a compound having an unsaturated group in a molecule and, moreover, having at least one carboxylic groups.

Specifically, there can be exemplified a compound represented by general formula (1) in addition to acrylic acid and methacrylic acid. In the general formula (1), "n" is an integer of 1–10, and $R^1$ is a hydrogen atom or a methyl group. X represents an alkylene group and, particularly preferably, an alkylene group having a carbon number of 1–3. The compound represented by the general formula (1) can be prepared by allowing to react a compound which is obtained by addition of E-caprolactone to hydroxyethyl(meth)acrylate with succinic acid, malonic acid, or adipic acid, etc.

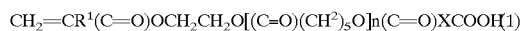

$$CH_2=CR^1(C=O)OCH_2CH_2O[(C=O)(CH^2)_5O]n(C=O)XCOOH \quad (1)$$

(in the general formula, "n" is an integer of 1–10, $R^1$ is a hydrogen atom or a methyl group. and X represents an alkylene group)

As the copolymerizable unsaturated carboxylic acid (Ua), acrylic acid and methacrylic acid are employed, which are usually employed.

<Unsaturated Compound (Ub)>

The unsaturated compound (Ub) other than the unsaturated carboxylic acid is a compound which is copolymerizable with the above-described unsaturated carboxylic acid (Ua), and there can be exemplified methyl(meth)acrylate, butyl(meth)acrylate, benzyl(meth)acrylate, cyclohexyl (meth)acrylate, and isobonyl(meth)acrylate, hydroxyethyl (meth)acrylate, further, esters of a compound represented by general formula (2), styrenes such as styrene and hydroxy styrene, maleic anhydride, and maleic acid imide, etc. In the general formula (2), "n" is an integer of 1–10, and $R^2$ is a hydrogen atom or a methyl group. The compound represented by the general formula (2) can be prepared by allowing to addition-react ∈-caprolactone to hydroxyethyl (meth)acrylate.

$$CH_2=CR^2(C=O)OCH_2CH_2O[(C=O)(CH^2)^5O]nH \quad (2)$$

(in the formula, "n" is an integer of 1–10, and $R^2$ is a hydrogen atom or a methyl group)

The unsaturated compound (Ub) other than the unsaturated carboxylic acid can be changed according to the use purpose, and a methacrylate and an acrylate are usually employed.

Constructing molar ratio of the copolymerizable unsaturated carboxylic acid (Ua) with respect to the unsaturated compound (Ub) other than the unsaturated carboxylic acid is 3:7–7:3, and preferably 6:4. In the case that the constructing molar ratio of the (a) with respect to (b) is in the above range, there is obtained a resin which is excellent in weatherability and adhesion.

<Epoxy group-contained Unsaturated Compound (Uc)>

The epoxy group-contained unsaturated compound (Uc) having a cycloaliphatic structure for adding to carboxylic groups which are side chains in a copolymer obtained is at least one of an unsaturated group-contained epoxy compound having a cycloaliphatic structure in the molecule and, there are enumerated 3,4-epoxycyclohexylmethyl methacrylate and a caprolactone-modified product thereof, and 3,4-epoxycyclohexylmethyl acrylate and a caprolactone-modified product thereof, etc.

These may be employed solely or in combination two or more kinds. By mixing the compound having a cycloaliphatic structure, water resistance and acid resistance are improved in a composition.

Use amount of the epoxy group-contained unsaturated compound (Uc) is 0.5–4.0 mol, particularly, preferably 1.0–3.5 mol as an amount of double bond derived from the epoxy group-contained unsaturated compound (Uc) based on 1 kg of a copolymer of the (Ua) with the (Ub).

In the case of less than 0.5 mol, sufficient curability cannot be occasionally obtained and, in the case of more than 4.0 mol, storage stability is occasionally poor. It is to be noted that carboxylic groups are preferably remained in the modified copolymer.

Polymerization reaction of the copolymerizable unsaturated carboxylic acid (Ua) with the unsaturated compound (Ub) other than the unsaturated carboxylic acid is conducted according to a usual method. After the preparation of a copolymer, the epoxy group-contained unsaturated compound (Uc) having a cycloaliphatic structure is added to carboxylic groups which are side chains in the copolymer obtained.

Addition reaction is preferably conducted at a temperature of not more than 130° C., and particularly, preferably 90–130° C. In the case of being lower than 90° C., practically sufficient reaction rate is not occasionally obtained and, in the case of being higher than 130° C., the double bonds are occasionally cross-linked in the modified copolymer (B') by thermally radical polymerization, resulting in that gelled substance is produced.

In the polymerization reaction and addition reaction, a solvent can be employed. The solvent for the reaction is not particularly limited, if it can dissolve raw materials and products. As a particularly preferred solvent, there may be employed a main solvent which is the above-described solvent (a) in view of a low toxicity and an excellent resist property, or a mixed solvent of the main solvent with the other solvent (c').

In the addition reaction, catalysts are preferably employed in order to obtain a sufficient reaction rate. As the catalysts, there can be employed phosphines such as triphenyl phosphine and tributyl phosphine, amines such as triethylamine and dimethylbenzyl amine, and sulphides such as dimethyl sulphide, etc., and the phosphines are preferred in view of reaction rate.

Use amount of the catalysts is preferably 0.01–10 parts by weight, and more preferably 0.5–5.0 parts by weight based on 100 parts by weight of the epoxy group-contained unsaturated compound (Uc) having a cycloaliphatic structure. In the case that the amount of the catalysts is less than 0.01 part by weight, a sufficient reaction rate is not occasionally obtained and, in the case of more than 10 parts by weight, it is anxious that a variety of properties are adversely affected in a resin produced.

In order to prevent generation of a gelled substance during the reaction, the addition reaction is preferably conducted under the presence of polymerization inhibitors such as hydroquinone, hydroquinone monomethylether, and phenothiazine. Amount of the polymerization inhibitors is preferably 1–10,000 ppm based on a total reaction liquid. In the case that the amount of the polymerization inhibitors is less than 1 ppm based on a total reaction liquid, a sufficient effect as a polymerization inhibitor is not occasionally obtained and, in the case of exceeding 10,000 ppm, it is anxious that a variety of properties are adversely affected in a resin produced. From the same reason, the addition reaction is preferably conducted under an atmosphere of a molecular-state oxygen-contained gas. Concentration of oxygen may be a concentration in which an explosive mixture is not formed in a reaction system and, it is usually adjusted to 1–7% by weight based on total reaction liquid.

<Resist Resin Composition (F')>

Use amount (concentration of a resist resin) of the modified copolymer (B') (hereinafter, occasionally referred to as "resist resin") depends upon a kind of the resist resin to be employed and main solvents to be employed, and it is 20–80% by weight based on total amount of the modified copolymer (B') and the solvent (A). In the case that the concentration of the resist resin is less than 20% by weight, a sufficient curing rate is not occasionally obtained in the use of a resist resin composition and, in the case of not less than 80% by weight, it is anxious that a coating layer becomes brittle because of excessive curing in the use.

<Reactive Diluent (C)>

In the photoresist resin composition (F'), there can be appropriately mixed the reactive diluent (C) having at least one (meth)acrylic group according to uses and physical properties of coating layer to be required, etc.

The reactive diluent (C) is not particularly limited, if it can dissolve the modified copolymer (B'). For example, there can be exemplified an alkyl or cycloalkyl(meth) acrylate such as isobonyl(meth)acrylate, cyclohexyl(meth) acrylate, and octyl(meth)acrylate; a hydroxyalkyl(meth) acrylate such as 2-hydroxyethyl(meth)acrylate and 3-hydroxypropyl (meth)acrylate; a mono or di(meth) acrylate such as ethylene glycol mono or di(meth)acrylate, methoxyethylene glycol(meth)acrylate, tetraethylene glycol mono or di(meth)acrylate, and tripropylene glycol mono or di(meth)acrylate; an epoxy group-contained (meth)acrylate such as 3,4-epoxycyclohexylmethyl(meth)acrylate and glycidyl(meth)acrylate; a (meth)acrylate of a polyol such as glycerine di(meth)acrylate, trimethylolpropane tri(meth) acrylate, pentaerythritol tri or tetra(meth)acrylate, and dipentaerythritol hexa(meth)acrylate, or a di(meth)acrylate of a polyalkylene glycol such as polyethylene glycol or polypropylene glycol, etc. Of those, there is preferred a (meth)acrylate having an ignition point of not less than 100° C. from a viewpoint of ensuring safeness in a preparation step thereof.

The reactive diluent (C) is formulated in a proportion of 1–150 parts by weight based on 100 parts by weight of the modified copolymer (B').

<Polymerization Initiator (D), etc.>

In the resist resin composition (F') of the present invention, the polymerization initiator (D) is formulated. The polymerization initiator (D) is not limited, and there can be employed benzoins, acetophenones, ketals, benzophenones, xanthones, and peroxides, etc. which are publicly-known and common.

The polymerization initiator is preferably formulated in a proportion of 1–10% by weight in a curable resin composition.

In the photoresist resin composition (F') to be employed in the present invention, there can be optionally formulated a reactive resin such as an epoxy resin, fillers such as barium sulphate, silicone oxide, talc, clay, and calcium carbonate, a coloring pigment such as Phthalocyanine green, Crystalviolet, titanium oxide, and carbon black, a variety of additives such as an adhesion agent and a leveling agent, and a polymerization inhibitor such as hydroquinone, hydroquinone monomethylether, and phenothiazine, etc.

A conventional low purity 3-alkoxy-1-propanol, particularly, 3-methoxy-1-propanol contains a large amount of alcoholic impurities. Accordingly, in the case that it is employed as a solvent for a curable resin such as a photoresist, since evaporation order from a coating layer is different, the coating layer does not become, for example, a uniform coating layer having a stable quality. For example, in the case that an alcohol having a low boiling point is contained, a uniform coating layer cannot be obtained because of accelerated drying in surface alone.

Particularly, methanol having a low boiling point largely affects to formation of a coating layer and, since it is a poisonous compound, a working circumstance must be severely controlled.

Further, methanol has a corrosion behavior for a copper thin layer which is employed for a resist.

On the other hand, since alcoholic impurities having a high boiling point such as 2-methyl-1-pentanol are apt to remain in a coating layer even though being baked, a delicate resist layer is not apt to be obtained in formation of the coating layer.

Further, since 3-methoxy-1-propanol is often employed in mixing with 1,3-propanediol methyletheracetate, etc., an another substance is occasionally produced by transesterification, etc. in the use at a high temperature such as baking, and it possibly causes a change of a pot life in the above-described curable resin solution.

On the other hand, in the high purity 3-alkoxy-1-propanol of the present invention, particularly, a high purity 3-methoxy-1-propanol, the above problems are reduced, and since it is apt to be employed by recycling, it has a merit also from a viewpoint of a working circumstance and environmental protection, and a coating layer made from the above-described curable resin solution is uniform and delicate.

EXAMPLES

Hereinafter, although the present invention is more specifically illustrated by Examples, the present invention is not limited by the Examples.

It is to be noted that "%" is shown by "% by weight" not so far as being particularly shown.

Hereinafter, the present invention No. I will be specifically illustrated.

As a reaction vessel, there was employed a tank-type reaction vessel (manufactured by SUS 316) having a capacity of 10 liter, equipped with a jacket and an agitator.

As a reaction vessel for a high pressure hydrogenation, there was employed a bubbling column-type reaction vessel (manufactured by SUS 316) equipped with a jacket.

As a distillation apparatus, there was employed a glass-made Oldarshaw-type distillation column (40 stages) equipped with a glass-made vacuum jacket.

<Analysis Method>

(1) Water Content

It was measured by according to JIS K0068 using a Karl Fischer's method.

(2) Gas Chromatographic (GC) Analysis

Apparatus: HP6890 (manufactured by Hewlett Packard, Ltd.)

Detector: FID

Capillary column: DB-WAX (manufactured by J&W, Ltd.) having 30 m×0.25 mm (layer thickness of 0.25 $\mu$m)

Carrier gas: Helium of 1.0 ml/minute (pressure of 12.1 psi), split ratio=1:100

Column temperature: 50–150° C. (temperature elevating rate of 5° C./minute)

Temperature at an inlet and detector: 250° C.

Sample amount introduced: 0.2 $\mu$l (neat sample)

Identification of components: Retention time (minute) is shown in a bracket.

Acrolein (2.54), methanol (2.85), 2-methyl-1-pentanol (9.80), 1,3-propnanediol methylether acetate (10.39), 3-methoxy-1-propaol (11.66), unknown components (2.29, 11.84, 12.00, 12.26, etc.).

Determination of components: Components to be identified are expressed in % by weight, and the amount of unknown components is expressed in % of area.

Example I-1

The reactor was continuously provided with a flow of acrolein (propionaldehyde concentration of 0.2% by weight) of 192 g/hour, a flow of methanol 1,081 g/hour, and a flow of an aqueous solution containing 5% by weight of NaOH of 2.2 g/hour. Reaction temperature was set up at 0° C., and raw materials were provided for 50 hours while the addition reaction was conducted. Reaction mass was obtained by overflowing the reactor and neutralized the overflowed mixture with an aqueous solution containing 20% of acetic acid. The reaction mass was then introduced into a hydrogenation reaction vessel. The reaction mass contained at a period of 40 hours after the introduction of the raw materials was analyzed by gas chromatography (GC), and the reaction mass contained 0.1% by weight of acrolein, 76.4% by weight of methanol, and 18.7% by weight of 3-methoxy-1-propanal. Conversion rate of acrolein was 99% and selectivity of 3-methoxy-1-propanal was 81%.

The above-mentioned reaction mass was continuously introduced into the high pressure hydrogenation reaction vessel for 50 hours, and a hydrogenation reaction was conducted under conditions of hydrogen pressure of 10 MPa, the reaction temperature of 130° C., and residence time of 1 hour. Raney's nickel was used as a catalyst for hydrogenation and continuously introduced in the amount of 3% by volume of the reaction mass. Crude reaction liquid resulting from hydrogenation was continuously discharged from the high pressure hydrogenation reaction vessel, and the catalyst was separated by filtration and the liquid was stored at room temperature. Raney's nickel was separated by filtration from the crude reaction liquid of hydrogenation obtained at a period of 40 hours after the introduction of the raw materials, and a filtrate was analyzed by GC. The filtrate contained 75.5% by weight of methanol, and 18.9% by weight of 3-methoxy-1-propanol, and 0.02% by weight of 2-methyl-1-pentanol. Conversion rate of 3-methoxy-1-propanal and selectivity of 3-methoxy-1-propanol were both 100%. According to infrared absorption spectra (IR) of the filtrate, absorption derived from aldehyde was not observed.

3,500 g of the stored crude hydrogenation reaction liquid was introduced into a bottom flask of a distillation apparatus and a batch distillation was then conducted. A distillate fraction of 500 g of 3-methoxy-1-propanol was obtained. As results of a gas chromatograph analysis, the composition of the distillate fraction was 99.8% by weight of 3-methoxy-1-propanol and 0.07% by weight of 2-methyl-1-pentanol. FIG. 1 shows a gas chromatogram.

Comparative Example I-1

The reactor was continuously provided with a flow of acrolein (propionaldehyde concentration of 1.5% by weight) of 192 g/hour, a flow of methanol 1081 g/hour, and a flow of an aqueous solution containing 5% by weight of NaOH of 2.2 g/hour. Reaction was performed under the same conditions as explained in the Example I-1. Reaction mass obtained at a period of 40 hours after the introduction of the raw materials was analyzed by gas chromatography (GC), and the reaction mass contained 0.1% by weight of acrolein, 76.4% by weight of methanol, and 18.6% by weight of 3-methoxy-1-propanal. Conversion of acrolein was 99%, and selectivity of 3-methoxy-1-propanal was 80%, respectively.

The above-mentioned reaction mass was then submitted to a hydrogenation reaction under the same conditions as explained in the Example I-1. Raney's nickel was separated by filtration from the crude reaction liquid of hydrogenation obtained at a period of 40 hours after the introduction of the raw materials and a filtrate was analyzed by GC. The filtrate contained 75.5% by weight of methanol, and 18.9% by weight of 3-methoxy-1-propanol, and 0.1% by weight of 2-methyl-1-pentanol. Conversion of 3-methoxy-1-propanal and selectivity of 3-methoxy-1-propanol were both 100%, respectively. According to an IR analysis, absorption derived from aldehyde was not observed.

3,500 g of the stored crude hydrogenation reaction liquid was introduced into a bottom flask of a distillation apparatus and a batch distillation was then conducted. A distillate fraction of 500 g of 3-methoxy-1-propanol was obtained. As results of the GC analysis, the composition of the fraction was 99.3% by weight of 3-methoxy-1-propanol and 0.5% by weight of 2-methyl-1-pentanol.

Comparative Example I-2

The reactor was continuously provided with a flow of acrolein (propionaldehyde concentration of 0.2% by weight) of 192 g/hour, a flow of methanol 1081 g/hour, and a flow of an aqueous solution containing 5% by weight of NaOH of 2.2 g/hour. Reaction was performed under the same conditions as explained in the Example I-1. Reaction mass obtained at a period of 40 hours after the introduction of the raw materials was analyzed by gas chromatography (GC), and the reaction mass contained 0.1% by weight of acrolein, 76.4% by weight of methanol, and 18.7% by weight of 3-methoxy-1-propanal. Conversion of acrolein was 99%, and selectivity of 3-methoxy-1-propanal was 81%, respectively.

The above-mentioned reaction mass was then submitted to a hydrogenation reaction under the same conditions as explained in the Example I-1 except that the reaction temperature was of 60° C.

Raney's nickel was separated by filtration from the crude reaction liquid of hydrogenation obtained at a period of 40 hours after the introduction of the raw materials and a filtrate was analyzed by GC. The filtrate contained 75.5% by weight of methanol, and 18.2% by weight of 3-methoxy-1-propanol, 0.7% by weight of 3-methoxy-1-propanal, and 0.02% by weight of 2-methyl-1-pentanol.

Conversion of 3-methoxy-1-propanal was 96% and selectivity of 3-methoxy-1-propanol was 100%, respectively.

3,500 g of the stored crude hydrogenation reaction liquid was likewise submitted to a batch distillation as in the Example I-1 to obtain a distillate fraction of 500 g of 3-methoxy-1-propanol. As results of the GC analysis, the composition of the distillate fraction was 99.2% by weight of 3-methoxy-1-propanol and 0.07% by weight of 2-methyl-1-pentanol, and methanol of 0.4% by weight.

Example I-2

The same reaction as described in the Example I-1 was performed except that ethanol was used instead of methanol in the same mol amount.

Crude hydrogenation reaction liquid obtained was provided in the bottom flask of the distillation apparatus and a batch distillation was performed to obtain a distillate of 3-ethoxy-1-propanol. As a gas chromatographic analysis, composition of the distillate was 99.9% by weight of 3-methoxy-1-propanol, ethanol of 0.01% by weight, and 0.03% by weight of 2-methyl-1-pentanol.

Reference Example I-1

11.0 mol of acetic anhydride was added to 10.0 mol of a high purity 3-methoxy-1-propanol obtained in the Example I-1. Resulting mixture was heated in the presence of an acidic ion-exchange resin and allowed to react to synthesize 1,3-propanediol methylether acetate.

The ion-exchange resin was separated from a synthesized liquid and after removing acetic acid and unreacted acetic anhydride, the liquid was purified by distillation to obtain a high purity 1,3-propanediol methylether acetate. As a result of a gas chromatographic analysis, composition of distillate was not less than 99.7% by weight of 1,3-propanediol methylether acetate, 0.01% by weight of methanol, and 0.01% by weight of 2-methyl-1-pentanol.

<Possibility of Utilization of the Present Invention No. I in Industry>

According to the present invention No. I, it is possible to efficiently produce a very high purity 3-alkoxy-1-propanol containing not more than 0.03% by weight of alcoholic impurities, which is very important as a raw material for drugs, pepticides, and as a solvent, etc.

In the present invention Nos. II–V described hereinafter, when the concentration of impurities is not expressly specified, 3-methoxy-1-propanol and 1,3-propanediol methylether acetate obtained in the present invention No. I were used.

Hereinafter, the present invention No. II is more specifically illustrated by Examples.

Preparation Example II-1

Preparation of a Resist Composition

A resist composition was prepared by dissolving 100 parts by weight of a novolak resin described hereinafter and 24 parts by weight of quinone diazide which is a photosensitive agent using propyleneglycol monomethyletheracetate (PGMEA) which is a solvent, so that a solid content becomes 25% by weight.

Novolak resin: m-cresol/p-cresol=6/4 (weight ratio) and a condensed polymer of formaldehyde.

Quinone diazide which is a photosensitive agent: an esterified product of 2,3,4,4'-tetrahydroxybenzophenone with 1,2-naphtoquinonediazide-5-sulphonyl chloride.

Examples II-1 to II-16

A composition prepared in the Preparation Example II-1 was spin-coated on a silicone base plate of 4 inches to form a resist layer having thickness of 2 μm after prebaking at 100° C. for 90 seconds using a direct hot plate. It is to be noted that in the Examples, the thickness of the resist layer was greater than the thickness of a layer usually employed in order to perform a dissolution test.

The resist layer obtained was submitted to the following dissolution test using the mixtures having a different mixing ratio shown in Table II-1 as a cleaning agent. Results of the tests are shown in the Table II-1.

Dissolution Test

The above-mentioned plate which is covered by the resist layer was soaked in 50 ml of a cleaning agent and the time (sec) through which the resist layer is completely dissolved was visually measured. Dissolution rate of the resist layer is shown as "Å/sec" which is calculated by dividing the thickness (Å) of the resist layer with the dissolution time (sec).

Comparative Examples II-1 to II-5

The same procedures were likewise followed as in the Example II-1 except that propyleneglycol monomethyletheracetate (PGMEA), propylene glycol methylether (PGMEA), 1-propanol (1-PA), ethylacetate (El), and ethanol were respectively used solely as a cleaning agent. Results are shown in Table II-1.

TABLE II-1

|  | Composition ratio of cleaning agent = weight % ratio |  | Dissolution rate (Å/sec) |
| --- | --- | --- | --- |
| Example II-1 | 1,3-PDMEA | =100 | 5000 |
| Example II-2 | 1,3-PDMEA: ethanol | =80:20 | 18000 |
| Example II-3 | 1,3-PDMEA: ethanol | =60:40 | 21000 |
| Example II-4 | 1,3-PDMEA: ethanol | =50:50 | 14000 |
| Example II-5 | 1,3-PDMEA: PGMEA: ethanol | =60:30:10 | 11500 |
| Example II-6 | 1,3-PDMEA: PGMEA: ethanol | =60:10:30 | 19800 |
| Example II-7 | 1,3-PDMEA: 1-PA | =80:20 | 7200 |
| Example II-8 | 1,3-PDMEA: 1-PA | =60:40 | 7600 |
| Example II-9 | 1,3-PDMEA: 1-PA | =50:50 | 5000 |
| Example II-10 | 1,3-PDME | =100 | 6900 |
| Example II-11 | 1,3-PDME: ethanol | =60:40 | 16600 |
| Example II-12 | 1,3-PDME: 1-PA | =60:40 | 12300 |
| Example II-13 | 1,3-PDME: PGMEA | =60:40 | 8500 |
| Example II-14 | 1,3-PDME: PGME | =60:40 | 7200 |
| Example II-15 | 1,3-PDME: EL | =60:40 | 9500 |
| Example II-16 | 1,3-PDME: 1,3-PDMEA | =50:50 | 10200 |
| Comparative Example II-1 | PGMEA | =100 | 2600 |
| Comparative Example II-2 | PGME | =100 | 4900 |
| Comparative Example II-3 | 1-PA | =100 | undissolved |
| Comparative Example II-4 | EL | =100 | 800 |
| Comparative Example II-5 | ethanol | =100 | undissolved |

Abbreviations in the Table
1,3-PDME: 1,3-propanediol methylether
1,3-PDMEA: 1,3-propanediol methyletheracetate
PGMEA: propyleneglycol methyletheracetate
PGME: propyleneglycol methylether As clearly shown in the Table II-1, it is confirmed that dissolution rate largely increases by mixing PGMEA, PGME, ethanol, 1-PA, and EL, etc. with 1,3-PDME and/or 1,3-PDMEA.

Examples II-17 to II-23

A resist was prepared by dissolving 100 parts by weight of an adamantine-based acrylic resin described below and 15 parts by weight of triphenyl sulphonium hexafuluoro antimony which is an acid-producing agent in ethyl lactate so that solid content becomes 25% by weight. The resist was spin-coated on a silicone base plate having 4 inches so that layer thickness becomes 2 μm after prebaking to prepare a resist layer by prebaking at 100° C. for 90 seconds using a direct hot plate.

Adamantine-based acrylic resin: a polymer having composition ratio of 50:50, a weight average molecular weight of 5,400, and a molecular weight distribution degree of 1.9 which is obtained by copolymerization of monohydroxyadamantyl acrylate with t-butylmethacrylate [structural formula (II-1) (1)].

Acid-producing agent: triphenyl sulphonium hexafuluoro antimony having a structural formula (II-1) (2).

Structural formula II-1
(1) Adamantine-based Acrylic Resin

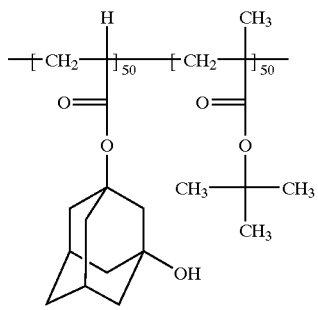

(2) Triphenyl Sulphonium Hexafuluoro Antimony

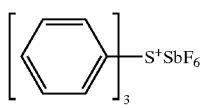

The resist layer prepared was employed for the following dissolution test using the mixtures having a different mixing ratio shown in Table II-2 as a cleaning agent. Results of the test are shown in Table II-2.

Dissolution Test

The above-mentioned plate which is covered by the resist layer was soaked in 50 ml of a cleaning agent and the time (sec) through which the resist layer is completely dissolved was visually measured. Dissolution rate of the resist layer is shown as "Å/sec" which is calculated by dividing the thickness (Å) of the resist layer with the dissolution time (sec).

Comparative Example II-1

The same procedures were likewise followed as in the Example II-17 except that PGMEA, PGMEA, EL, 1-PA, and ethanol were respectively used solely as a cleaning agent. Results are shown in Table II-2.

TABLE II-2

|  | Composition ratio of cleaning agent = mass ratio |  | Dissolution rate (Å/sec) |
| --- | --- | --- | --- |
| Example II-17 | 1,3-PDMEA | =100 | 4300 |
| Example II-18 | 1,3-PDMEA: ethanol | =60:20 | 10900 |
| Example II-19 | 1,3-PDMEA: PGMEA: ethanol | =60:10:30 | 12500 |
| Example II-20 | 1,3-PDMEA: I-PA | =60:40 | 11300 |
| Example II-21 | 1,3-PDME | =100 | 5700 |
| Example II-22 | 1,3-PDME: ethanol | =60:40 | 10600 |
| Example II-23 | 1,3-PDMEA: 1-PA | =60:40 | 9800 |
| Comparative Example II-6 | PGMEA | =100 | 2400 |
| Comparative Example II-7 | PGME | =100 | 3200 |
| Comparative Example II-8 | EL | =100 | 3900 |
| Comparative Example II-9 | 1-PA | =100 | undissolved |
| Comparative Example II-10 | ethanol | =100 | undissolved |

Abbreviations in the Table
1,3-PDME: 1,3-propanediol methylether

TABLE II-2-continued

| Composition ratio of cleaning agent = mass ratio | Dissolution rate (Å/sec) |
|---|---|

1,3-PDMEA: 1,3-propanediol methyletheracetate
PGMEA: propyleneglycol methyletheracetate
PGME: propyleneglycol methylether As clearly shown in the Table II-1, it is confirmed that dissolution rate largely increases by mixing PGMEA, PGME, ethanol, 1-PA, and EL, etc. with 1,3-PDME and/or 1,3-PDMEA.

<Possibility of Utilization of the Present Invention No. II in Industry>

According to the present invention No. II, it is possible to greatly increase solubility into a resist, etc. compared to conventional cleaning agents. Further, it is possible to obtain a cleaning agent for lithography having a very high safeness, and it is possible to conduct a sufficient cleaning by a small amount of cleaning agent within a short cleaning time of period.

Hereinafter, the present invention No. III is more specifically illustrated by Examples.

Example III-1

A resist composition prepared in the Preparation Example II-1 was spin-coated on a silicone base plate of 4 inches to form a resist layer having thickness of 2.6 μm after prebaking at 100° C. for 90 seconds using a direct hot plate. It is to be noted that in the Examples, the thickness of the resist layer was greater than the thickness of a layer usually employed in order to perform a dissolution test.

The resist layer prepared was submitted to the following dissolution test using rinse liquids 1-(1) to 1-(8) composed of the mixed solvents (Solvent A) shown in Table III-1 and water. Results are shown in the Table III-1.

(Dissolution Test)

0.03 ml of the rinsing liquids were dropped on the above-mentioned resist layer, and a time (sec) was measured until the silicone which is an under layer can be seen. Dissolution rate of the resist layer is shown as "Å/sec" which is calculated by dividing the thickness (Å) of the resist layer with the time (sec).

Comparative Examples III-1

The same procedures were likewise followed as in the Example III-1 except that the solvent A alone was used as a rinsing liquid, in which water is not mixed. Results are shown in Table III-1.

TABLE III-1

| Rinsing liquid | Composition of rinsing liquid (part by mass) | | Dissolution rate (Å/sec) |
|---|---|---|---|
| | Mixed organic solvent (Solvent A) | water | |
| Example III-1 (1) | 1,3-PDME: 1,3-PDMEA =50:50 | 5 | 13,900 |
| Example III-1 (2) | 1,3-PDME: 1,3-PDMEA =50:50 | 10 | 14,400 |
| Example III-1 (3) | 1,3-PDME: 1,3-PDMEA =50:50 | 15 | 14,600 |
| Example III-1 (4) | I,3-PDME: 1,3-PDMEA =50:50 | 20 | 13,700 |
| Example III-1 (6) | 1,3-PDME: 1,3-PDMEA =50:50 | 30 | 13,200 |
| Example III-1 (7) | 1,3-PDME: 1,3-PDMEA =50:50 | 50 | 12,800 |

TABLE III-1-continued

| Rinsing liquid | Composition of rinsing liquid (part by mass) | | Dissolution rate (Å/sec) |
|---|---|---|---|
| | Mixed organic solvent (Solvent A) | water | |
| Example III-1 (8) | 1,3-PDME: 1,3-PDMEA =50:50 | 100 | 12,300 |
| Comparative Example III-1 | 1,3-PDME: 1,3-PDMEA =50:50 | 0 | 11,600 |

Abbreviations in the Table
1,3-PDME: 1,3-propanediol methylether
1,3-PDMEA: 1,3-propanediol methylether acetate As clearly shown in the Table 1, it is confirmed that dissolution rate largely increases by adding water to a mixture composed of 1,3-propanediol methylether and 1,3-propanediol methylether acetate.

Examples III-2

1 part of polyvinylpyrrolidone, 4 parts of perfuluorooctane sulphonate, 0.35 part of 2-aminoethanol, 0.004 part of a water-soluble alkyl siloxane polymer (Polyflow-KL-245 manufactured by Kyoeisya Yushi, Ltd.), and 94.646 parts of pure water were mixed together to prepare a composition to be used in order to prepare a reflection-protecting layer. The composition was spin-coated on a 4-inches silicone plate and baked up at 90° C. for 90 seconds to form a reflection-protecting layer having a thickness of 650 Å. Each of the rinsing liquids shown in Table III-1 was dropped on the reflection-protecting layer. At immediately after dropwise addition of the rinsing liquids, contact angle was reduced and the rinsing liquid has a good affinity to the reflection-protecting layer, and smooth dissolution was attained compared to the rinsing liquid which does not contain water.

<Possibility of Utilization of the Present Invention No. III in Industry>

According to the present Invention No. III, solubility to a resist layer and a reflection-protecting layer, etc. is elevated compared to a case in which a conventional water-soluble organic solvent alone is employed as a rinsing liquid, and rinsing liquids have a good affinity to a layer prepared from an aqueous solution and smoothly dissolves.

Further, since the rinsing liquids contain water, an ignition point elevates in the rinsing liquids, and a regulation by a Fire Protecting Law in Japan, etc. becomes loosened, resulting in that there is an effect that handling becomes easy in a production site and a plant.

Hereinafter, the present invention No. IV is more specifically illustrated by Examples.

Examples IV-1 to IV-5

1 mol of 2,2'4,4'-tetrahydroxybenzophenone and 3 mol of naphtoquinone-1,2-diazide-5-sulphonyl chloride were submitted to an esterification reaction to obtain of a product. 2 g of the product and 8 g of a cresol novolak resin were dissolved in solvents shown in Table 1 so that a solid content becomes 25% by weight to prepare a coating liquid of a positive type photoresist composition. Physical properties of thus-obtained coating liquids were measured, and results are shown in Table IV-1.

Comparative Examples IV-1 to IV-3

The same procedures were likewise followed as in the Example IV-1 except that propyleneglycol monomethylether acetate (PGMEA), cyclopentanone, and ethyl lactate were employed instead of the solvents employed in the Examples. Physical properties are shown in Table IV-1.

It is to be noted that the physical properties in the Table were measured as follows.

Presence or absence of a precipitate: Coating liquid prepared was filtered by a 0.2 μm-membrane filter and placed at 40° C., and the presence or the absence of a precipitate in the coating liquid was measured.

Change of sensitivity: Presence or absence of the change of sensitivity was measured in a photoresist composition after 3 months.

Shape of a cross-section: Coating liquid prepared was spin-coated on a 6-inches silicone wafer and dried at 90° C. for 90 seconds by a hot plate to form a resist layer having thickness of 1.3 μm.

The layer was exposed to light through a fixed mask using a stepper, followed by heating on a hot plate at 110° C. for 90 seconds, and then by developing using 2.38%-aqueous solution of tetramethylammonium hydroxide (TMAH). Shape of a cross-section of a resist pattern obtained by cleaning-drying for 30 seconds was visually observed and evaluated by the following standards.

○: no penetration in a contact zone between the silicone wafer and the resist pattern.

X: penetration in a contact zone between the silicone wafer and the resist pattern.

Novolak resin: m-cresol/p-cresol=4/6 (by weight) and a condensed polymer of formaldehyde.

TABLE IV-2

| | Solvent for a resist (mass % in mixing) |
|---|---|
| Example IV-6 | 1,3-PDMEA = 100 |
| Example IV-7 | 1,3-PDMEA:1,3-PDME = 50:50 |
| Example IV-8 | 1,3-PDMEA:PGMEA = 60:40 |
| Example IV-9 | 1,3-PDMEA:PGME = 60:40 |
| Example IV-10 | 1,3-PDMEA:EL = 60:40 |
| Example IV-11 | 1,3-PDME = 100 |
| Example IV-12 | 1,3-PDME:MBAC = 60:40 |
| Comparative Example IV-4 | PGMEA = 100 |
| Comparative Example IV-5 | PGMEA:PnB = 80:20 |

MBAC: 3-methoxy-butylacetate
PnB: butyl propionate

Ratio of remaining solvent was for thus-prepared resist composition conducted by the following method to obtain results shown in Table IV-3.

Ratio of remaining solvent: Thickness of the resist layer is thin which is actually coated on a base plate. For that reason, absolute amount of the solvent is small, accordingly, a fair amount of the solvent evaporates even by a spin-coating alone before prebaking, and evaporation rate of the solvent is also quick,

TABLE IV-1

| | Solvent composition | | P or A | | C of S | |
|---|---|---|---|---|---|---|
| | (weight % in mixing) | | 1-M | 2-M | 3-M | S of CS |
| Example IV-1 | 1,3-PDMEA | =100 | A | A | A | ○ |
| Example IV-2 | 1,3-PDMEA: 1,3-PDME | =60:40 | A | A | A | ○ |
| Example IV-3 | 1,3-PDMEA: PGMEA | =60:40 | A | A | A | ○ |
| Example IV-4 | 1,3-PDMEA: EL | =60:40 | A | A | A | ○ |
| Example IV-5 | 1,3-PDMEA: MAK | =60:40 | A | A | A | ○ |
| Comparative Example IV-1 | PGMEA | =100 | A | P | A | x |
| Comparative Example IV-2 | CPANON | =100 | A | A | P | x |
| Comparative Example IV-3 | EL | =100 | A | P | A | x |

Abbreviations in the Table
1,3-PDMEA: 1,3-propanediol methylether acetate
1,3-PDME: 1,3-propanediol methylether
PGMEA: propyleneglycol methylether acetate
EL: ethyl lactate
NAK: methylamyl ketone
CPANON: cyclopentanone
P or A: presence or absence
C of S: change of sensitivity
S of CS: shape of cross-section
M: month Examples IV-6 to IV-12, Comparative Examples IV-4 to IV-5

Resist composition in the Examples IV-6 to IV-12 and Comparative Examples IV-4 to IV-5 was prepared as follows.

Quinone diazide which is a photosensitive agent and the novolak resin which are described below were dissolved in a proportion of 24 parts by weight of quinone diazide based on 100 parts by weight of the novolak resin into solvents having the composition described at respective Examples and Comparative Examples in Table IV-2, so that solid component thereof becomes 25% by weight.

Quinone diazide which is a photosensitive agent: an esterified product of 2,2,4,4'-tetrahydroxybenzophenone with 1,2-naphtoquinonediazide-5-sulphonyl chloride.

Accordingly, it is difficult to directly measure the amount of the remaining solvent. For that reason, the following modeling tests were conducted to calculate the ratio of remaining solvent in the resist layer after prebaking. That is, 2.0000 g of 9 kinds of the resist compositions in the Examples IV-1 to IV-7 and Comparative Examples IV-1 and IV-2 were used to uniformly cover the bottom of an aluminum Petri dish having the same diameter, followed by heating on a hot plate at 100° C. for 2–30 minutes and by measuring respective weight and calculating the ratio of remaining solvent by the following formula. Results are shown in Table IV-3.

Ratio of remaining solvent={[(total weight after heating for a fixed time of period)−(weight of Petri dish)−(weight of solid components in a resist)]/(solvent weight before baking)}×100 (%)

However, since 2,000 g of the resist composition was used and solid components concentration is 25% by weight, the amount of solid components in the resist is 500 g, and the weight of solvent before baking is 1,500 g.

TABLE IV-3

| | Baking time of period (minute) | | | | | |
|---|---|---|---|---|---|---|
| | 2 | 5 | 10 | 15 | 20 | 30 |
| Example IV-1 | 82.6 | 57.9 | 38.8 | 30.9 | 26.2 | 20.5 |
| Example IV-2 | 78.1 | 53.4 | 36.9 | 28.9 | 25.2 | 19.6 |
| Example IV-3 | 81.1 | 57.1 | 37.8 | 30.2 | 36.0 | 20.5 |
| Example IV-4 | 80.0 | 55.4 | 37.3 | 29.1 | 25.8 | 20.1 |
| Example IV-5 | 79.8 | 54.3 | 37.3 | 29.4 | 25.4 | 19.8 |
| Example IV-6 | 81.9 | 57.3 | 38.2 | 30.4 | 26.1 | 20.4 |
| Example IV-7 | 80.9 | 56.9 | 37.6 | 29.8 | 25.7 | 20.3 |
| Comparative Example IV-1 | 77.3 | 52.9 | 36.3 | 31.1 | 27.8 | 23.7 |
| Comparative Example IV-2 | 80.1 | 55.7 | 37.2 | 29.3 | 26.7 | 22.2 |

In the tests for measuring the ratio of remaining solvent, since a resist is more thickly coated compared to a layer thickness of a usual resist, as it were, those are a modeling test.

Accordingly, the baking duration determined in the tests cannot be the same as the baking duration used in a real process.

In a practical baking state in which the ratio of remaining solvent is relatively lower such as not more than 30% by weight, and adhesion to a base plate during development can be kept, that is, in the tests, it is possible to consider while comparing the Examples with the Comparative Examples concerning the data including a baking duration of not less than 15 minutes in the above-described tests. And, from the above results, it was confirmed that the ratio of remaining solvent in a practical baking duration is lower in the Examples that in the Comparative Examples.

In the practical baking duration, the ratio of remaining solvent becomes not more than 30% by weight, that is, it was confirmed that it is excellent in an evaporation property.

The reason for this depends upon that due to the use of 1,3-PDME or 1,3-PDMEA, or a mixture thereof, etc. together with EL, MBAC, etc. in suitable proportions, the formation rate of a skin layer on the surface of the resist layer is low and thus evaporation of the solvent can smoothly take place.

Examples IV-13 to IV-15 and Comparative Example IV-6

Resist compositions for the Examples IV-13 to IV-15 and Comparative Example IV-6 were prepared as follows.

Monohydroxy adamantine acrylate and tetrahydropyranyl methacrylate were copolymerized to obtain a copolymer containing 70% by mol of monohydroxy adamantine acrylate and 30% by mol of tetrahydropyranyl methacrylate, and which has a weight average molecular weight of 8,000. The copolymer was dissolved in solvents having a composition described at a section of the Examples and Comparative Examples in Table IV-4, so that solid components becomes 25% by weight.

Solubility of a resin: Solvent was added to the resin prepared so that the concentration of solid components becomes 25% by weight, followed by heating to 50° C. over 10 minutes. The solubility of a resin was evaluated according to the following standards.

○: Homogeneous and transparent liquid was obtained.

X: Particle-state insoluble resin was remained on the wall of apparatus.

TABLE IV-4

| | Solvent for a resist (mass % in mixing) | Solubility of a resin |
|---|---|---|
| Example IV-13 | 1,3-PDMEA = 100 | ○ |
| Example IV-14 | 1,3-PDMEA:1,3-PDME = 50:50 | ○ |
| Example IV-15 | 1,3-PDMEA:EL = 60:40 | ○ |
| Comparative Example IV-6 | PGMEA = 100 | X |

<Possibility of Utilization of the Present Invention No. IV in Industry>

According to the present Invention No. IV, it was confirmed that the solvents for a resist composition is excellent in safeness to human body and, further, it is excellent in solubility to a resist and coatability, and the ratio of remaining solvent is improved. Still further, the resist solution prepared has an effect of an excellent stability, and it is particularly useful as a resist composition for manufacturing a semiconductor device or a liquid crystal element, etc.

Hereinafter, the present invention No. V is more specifically illustrated by Examples.

Preparation Example V-1

A separable flask equipped with an agitator, a thermometer, a condenser, and a tube for supplying nitrogen gas having an internal capacity of 5-liter was charged with 600 g of propyleneglycol monomethylether and 10 g of t-butyl-peroxy-2-ethylhexanoate. After elevating a temperature to 90° C., there was added dropwise a mixture composed of 200 g of methacrylic acid, 250 g of benzyl methacrylate, 300 g of propyleneglycol monomethylether, and 10 g of azobisdimethyl valeronitrile over 3 hours, followed by further aging for 6 hours to obtain a resin solution having carboxylic groups. Polymerization reaction was conducted under a nitrogen stream.

Subsequently, a solution of a modified copolymer (B'1) was obtained by allowing to react adding 425 g of 3,4-epoxycyclohexylmethylacrylate ("Cyclomer A200" manufactured by Daicel Chemical Industries, Ltd.), 45 g of triphenylphosphine, and 1.8 g of hydroquinone monomethylether at 100° C. for 20 hours. The addition reaction was conducted under a mixed gas stream composed of 7% by volume of oxygen and 93% by volume of nitrogen.

Examples V-1 to V-3

In the Examples V-1 to V-3, a coating liquid of a negative type photoresist resin composition was prepared by dissolving a formulating mixture composed of 100 parts by weight of the solution of the modified copolymer (B'1) prepared in the Preparation Example V-1, 50 parts by weight of trimethylolpropane triacrylate, and 2 parts by weight of "Irugacure 907" which is an initiator manufactured by Ciba-Geigy AG. into solvents shown in Table V-1, so that solid components becomes 25% by weight.

In the solvent 1,3-propanediol methylether employed, total amount of alcohol components such as methanol and 2-methyl-1-pentanol was 0.2% by weight and, in 1,3-propanediol methylether acetate, total amount of alcohol components such as methanol and 2-methyl-1-pentanol was 0.2% by weight.

Physical properties of the coating liquid obtained were measured, and results are shown in Table V-1.

Comparative Examples IV-1 to IV-3

The same procedures were likewise followed as in the Example V-1 except that propyleneglycol monomethyletheracetate (PGMEA), cyclopentanone or ethylacetate (EL) were respectively used as a solvent. Results are shown in Table V-1.

Physical properties in the Table were measured as follows.

(1) Presence or absence of a precipitate: Coating liquid prepared was filtered through a membrane filter having an aperture of 0.2 μm and placed at 40° C., and the presence or the absence of a precipitate in the coating liquid was measured.

(2) Change of sensitivity: Presence or absence of the change of sensitivity was measured in a photoresist composition after 3 months.

(3) Pattern formability: Resist pattern was observed by a microscope.

Evaluation results are shown by ⊚: most excellent, ○: excellent, and X: worse.

(4) Etching resistance: A copper-plated laminated board on which a pattern is formed was evaluated by etching with spraying of ferric chloride at 50° C.

Evaluation results are shown by ⊚: most excellent, ○: excellent, Δ: slightly excellent, and X: worse.

Herein, a resist pattern in which the pattern formability (3) and the etching resistance (4) are evaluated was obtained by coating-drying a coating liquid on a copper-plated laminated board in the thickness of 10 μm (thickness after drying at 80° C. and 10 minutes) using a barcoater and contact-exposing to light using a pattern film having line/line space=30 μm/30 μm, followed by developing by 1%-sodium carbonate.

TABLE V-1

| Solvent | | Precipitate | | | C of S | |
|---|---|---|---|---|---|---|
| | (weight ratio in mixing) | 1-M | 2-M | 3-M | PF | ER |
| Example V-1 | 1,3-PDME = 100 | A | A | A | ⊚ | ⊚ |
| Example V-2 | 1,3-PDMEA: 1,3-PDME= 60:40 | A | A | A | ⊚ | ⊚ |
| Example V-3 | 1,3-PDMEA: PGMEA = 60:40 | A | A | A | ○ | ○ |
| Comparative Example V-1 | PGMEA = 100 | A | P | P | ○ | Δ |
| Comparative Example V-2 | CPANON = 100 | P | P | P | X | X |
| Comparative Example V-3 | EL = 100 | P | P | P | X | X |

Abbreviations in the Table
1,3-PDMEA: 1,3-propanediol methyletheracetate
1,3-PDME: 1,3-propanediol methylether
PGMEA: propyleneglycol methylethoracetate
EL: ethyl lactate
CPANON: cyclopentanone
P or A: presence or absence
C of S: change of sensitivity
M: month
PF: Pattern formability
ER: Etching resistance

Examples V-4 to V-6 and Comparative Examples V-4 to V-6

Resist compositions for the Examples V-4 to V-6 and Comparative Examples V-4 to V-6 were prepared as follows. That is, 50 parts by weight of trimethylolpropane triacrylate and 2 parts by weight of "Irugacure 907" manufactured by Ciba Geigy AG. were formulated with 100 parts by weight of the modified copolymer (B'1) prepared in the Example V-1, followed by dissolving in the solvents having composition described at a section of Examples and Comparative Examples in Table V-1, respectively.

In relation to thus-prepared resist resin compositions, a test of the ratio of remaining solvent was measured by the following method (1). Results are shown in Table V-2.

TABLE V-2

| | Baking time of period (minute) | | | | | |
|---|---|---|---|---|---|---|
| | 2 | 5 | 10 | 15 | 20 | 30 |
| Example V-4 | 80.0 | 55.4 | 37.3 | 29.1 | 25.8 | 20.1 |
| Example V-5 | 79.8 | 54.3 | 37.3 | 29.4 | 25.4 | 19.8 |
| Example V-6 | 81.9 | 57.3 | 38.2 | 30.4 | 26.1 | 20.4 |
| Comparative Example V-4 | 80.9 | 56.9 | 37.6 | 29.8 | 25.7 | 20.3 |
| Comparative Example V-5 | 77.3 | 52.9 | 36.3 | 31.1 | 27.8 | 23.7 |
| Comparative Example V-6 | 80.1 | 55.7 | 37.2 | 29.3 | 26.7 | 22.2 |

(1) Ratio of remaining solvent: Thickness of the resist layer is thin which is actually coated on a base plate. For that reason, an absolute amount of the solvent is small, accordingly, a fair amount of the solvent evaporates even by a spin-coating alone before baking, and evaporation rate of the solvent is also quick, accordingly, it is difficult to directly measure the amount of the remaining solvent. For that reason, the following modeling tests were conducted to calculate the ratio of remaining solvent in the resist layer after prebaking. That is, 2.0000 g of 9 kinds of the resist compositions in the Examples V-4 to V-6 and Comparative Examples V-4 and V-6 were used to uniformly cover the bottom of an aluminum Petri dishes having the same diameter, followed by heating on a hot plate at 100° C. for 20–30 minutes and measuring respective weight and calculating the ratio of remaining solvent by the formula described in the present invention No. IV. Results are shown in Table V-2.

However, since 2.0000 g of the resist composition was used and solid components concentration is 25% by weight, the amount of solid components in the resist is 0.5000 g, and the weight of solvent before baking is 1.5000 g.

As an index for uniformity and delicateness, a pencil scratching test according to a JIS regulation was conducted in relation to a coating layer after curing, and scattering was measured in each position of the coating layer.

In the tests for measuring the ratio of remaining solvent, since a resist is more thickly coated compared to a layer thickness of a usual resist, as it were, those are a modeling test.

Accordingly, the baking duration determined in the tests cannot be the same as the baking duration used in a real process.

In a practical baking state in which the ratio of remaining solvent is relatively lower such as not more than 30% by weight, and adhesion to a base plate during development can be kept, that is, it is possible to consider while comparing the Examples with the Comparative Examples concerning the data including a baking duration of not less than 15 minutes in the above-described tests.

And, from the above results, it was confirmed that the ratio of remaining solvent in a practical baking duration is lower in the Examples that in the Comparative Examples. In the practical baking duration, the ratio of remaining solvent becomes not more than 30% by weight, that is, it was confirmed that it is excellent in an evaporation property. The reason for this depends upon that due to the use of 1,3-

PDME or 1,3-PDMEA, or a mixture thereof, etc. together with PGMEA, etc. in suitable proportions, the formation rate of a skin layer on the surface of the resist layer is low and thus evaporation of the solvent can smoothly take place.

Example V-7

The same procedures were likewise followed as in the Example V-4 except that 1,3-PDME having a high content of alcohols (methanol content of 0.25% by weight and 2-methyl-1-pentanol content of 0.15% by weight) was used. Results shown in Table V-3 were obtained in relation to uniformity and delicateness of a resist.

As a result, hardness of a coating layer is higher in the case (Example V-4) that the 1,3-PDME having a low content of alcohols is employed, and scattering in each position is also smaller compared to the case (Example V-4) that the 1,3-PDME having a high content of alcohols is employed.

TABLE V-3

|  | Pencil hardness in each position of a coating layer | | | | |
| --- | --- | --- | --- | --- | --- |
|  | a | b | c | d | e |
| Example V-4 | H | H | H | HB | H |
| Example V-7 | HB | B | HB | HB | B |

<Possibility of Utilization of the Present Invention No. V in Industry>

According to the present invention No. V, it was confirmed that the photoresist composition is excellent in view of safeness to human body and, further, it is excellent in solubility to a resist resin and coatability and, moreover, the ratio of remaining solvent is improved, and, particularly, a uniform and delicate coating layer can be obtained by the use of a specified solvent having a low alcohol content. Further, a solution of resist resin composition prepared according to the present invention is particularly useful as a liquid etching for preparing a printed circuit board and a solder photoresist resin composition.

What is claimed is:

1. A high purity liquid 3-alkoxy-1-propanol having not more than 0.3% by weight of alcoholic impurities.

2. A high purity 3-alkoxy-1-propanol as claimed in claim 1, wherein said 3-alkoxy-1-propanol is 3-methoxy-1-propanol.

3. A high purity 3-alkoxy-1-propanol as claimed in claim 2, wherein said alcoholic impurities are 2-methyl-1-pentanol and/or methanol.

4. A method for the preparation of a high purity 3-alkoxy-1-propanol characterized in that a 3-alkoxy-1-propanal is produced by allowing to react acrolein with a linear or branched alcohol having a carbon number of 1–4 using acrolein having the content of propionaldehyde of not more than 1% by weight as a raw material, and a 3-alkoxy-1-propanol is produced by a hydrogenation reaction of a reaction mass using hydrogen under the presence of a catalyst, followed by recovering through a distillation of said 3-alkoxy-1-propanol having the content of alcoholic impurities of not more than 0.3% by weight from a crude solution in the hydrogenation reaction.

5. A method for the preparation of a high purity 3-alkoxy-1-propanol as claimed in claim 4 characterized in that the concentration of a residual aldehyde compound in said crude solution is adjusted to not more than 0.5% by weight in the hydrogenation reaction.

6. A method for the preparation of a high purity 3-alkoxy-1-propanol as claimed in claim 4 or 5, wherein said 3-alkoxy-1-propanol is 3-methoxy-1-propanol.

7. A method for the preparation of a high purity 3-alkoxy-1-propanol as claimed in claim 6, wherein said alcoholic impurities are methanol and/or 2-methyl-1-pentanol.

* * * * *